United States Patent
Keitel et al.

(10) Patent No.: US 10,518,037 B2
(45) Date of Patent: Dec. 31, 2019

(54) INJECTION DEVICE

(71) Applicant: Haselmeier AG, St. Gallen (CH)

(72) Inventors: Joachim Keitel, Esslingen (DE);
Daniel MacDonald, Brossard (CA);
Herbert Bechtold, Denkingen (DE)

(73) Assignee: Haselmeier AG, St. Gallen (CH)

( * ) Notice: Subject to any disclaimer, the term of this patent is extended or adjusted under 35 U.S.C. 154(b) by 314 days.

(21) Appl. No.: 15/611,537

(22) Filed: Jun. 1, 2017

(65) Prior Publication Data

US 2017/0266387 A1 Sep. 21, 2017

Related U.S. Application Data

(63) Continuation of application No. 14/822,537, filed on Aug. 10, 2015, now Pat. No. 9,694,136, which is a (Continued)

(30) Foreign Application Priority Data

Feb. 8, 2013 (DE) .................... 20 2013 001 350 U

(51) Int. Cl.
*A61M 5/315* (2006.01)
*A61M 5/24* (2006.01)
*A61M 5/20* (2006.01)

(52) U.S. Cl.
CPC .... *A61M 5/31551* (2013.01); *A61M 5/31585* (2013.01); *A61M 5/24* (2013.01);
(Continued)

(58) Field of Classification Search
CPC .......... A61M 5/31551; A61M 5/31585; A61M 5/31543; A61M 5/3156
See application file for complete search history.

(56) References Cited

U.S. PATENT DOCUMENTS 7,611,491 B2 11/2009 Pickhard
7,686,786 B2 * 3/2010 Moller .............. A61M 5/14566
604/134

(Continued)

FOREIGN PATENT DOCUMENTS

EP 1610848 B1 10/2006
WO 2006/076921 A1 7/2006

(Continued)

OTHER PUBLICATIONS

Search Report issued in the European Patent Application No. 17001491.4 dated Jan. 22, 2018.

(Continued)

*Primary Examiner* — Andrew M Gilbert
(74) *Attorney, Agent, or Firm* — Walter Ottesen, P.A.

(57) ABSTRACT

An injection device includes a housing having a receptacle for a vessel for holding injection fluid; an operator-manipulated element for setting an injection dose; a dosing member rotatable about a longitudinal center axis relative to the housing when setting the injection dose; a feed part; and, a latching unit acting between the feed part and housing. The dosing member has a zero position whereat no dose is set and an injection position whereat an intended dose of injection fluid is set. A spring acts between the dosing member and the housing to return the dosing member from an intermediate position to the injection position or a zero position.

15 Claims, 16 Drawing Sheets

Related U.S. Application Data continuation of application No. PCT/EP2014/000313, filed on Feb. 5, 2014.

(52) U.S. Cl.
CPC ....... *A61M 5/3156* (2013.01); *A61M 5/31543* (2013.01); *A61M 2005/2026* (2013.01); *A61M 2205/581* (2013.01); *A61M 2205/582* (2013.01)

(56) References Cited

U.S. PATENT DOCUMENTS

| | | | |
|---|---|---|---|
| 8,096,978 B2* | 1/2012 | Markussen | A61M 5/20 604/135 |
| 8,585,658 B2 | 11/2013 | Forstreuter | |
| 8,663,167 B2 | 3/2014 | Bartha | |
| 8,747,367 B2* | 6/2014 | Keitel | A61M 5/31551 604/211 |
| 9,132,239 B2 | 9/2015 | Moeller et al. | |
| 9,533,106 B2* | 1/2017 | Hansen | A61M 5/20 |
| 9,694,136 B2* | 7/2017 | Keitel | A61M 5/31551 |
| 2004/0236285 A1 | 11/2004 | Fisher et al. | |
| 2005/0090782 A1* | 4/2005 | Marshall | A61M 5/31525 604/211 |
| 2005/0258988 A1 | 11/2005 | Jiang | |
| 2006/0276753 A1 | 12/2006 | Kronestedt et al. | |
| 2008/0306445 A1 | 12/2008 | Burren et al. | |
| 2012/0029443 A1 | 2/2012 | Holmqvist | |
| 2012/0184917 A1 | 7/2012 | Bom et al. | |
| 2013/0096513 A1* | 4/2013 | Smith | A61M 5/20 604/211 |
| 2015/0133869 A1 | 5/2015 | Streit et al. | |
| 2015/0133871 A1 | 5/2015 | Stefanski | |
| 2015/0148750 A1* | 5/2015 | Pedersen | A61M 5/20 604/207 |

FOREIGN PATENT DOCUMENTS

| | | |
|---|---|---|
| WO | 2010/140974 A1 | 12/2010 |
| WO | 2011/101349 A1 | 8/2011 |

OTHER PUBLICATIONS

English translation of the Decision for Granting a Patent for Invention of the Russian Patent Office dated Apr. 11, 2017 in the corresponding Russian patent application 2015132799/14(050432).
International Search Report dated May 12, 2014 of international application PCT/EP2014/000313 on which this application is based.

* cited by examiner

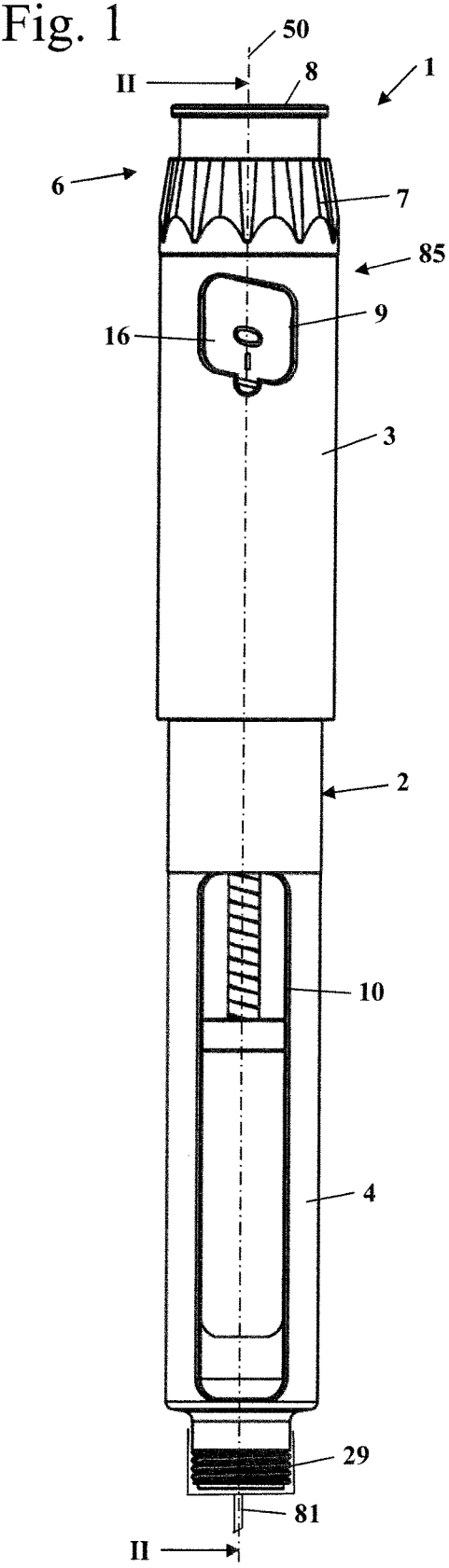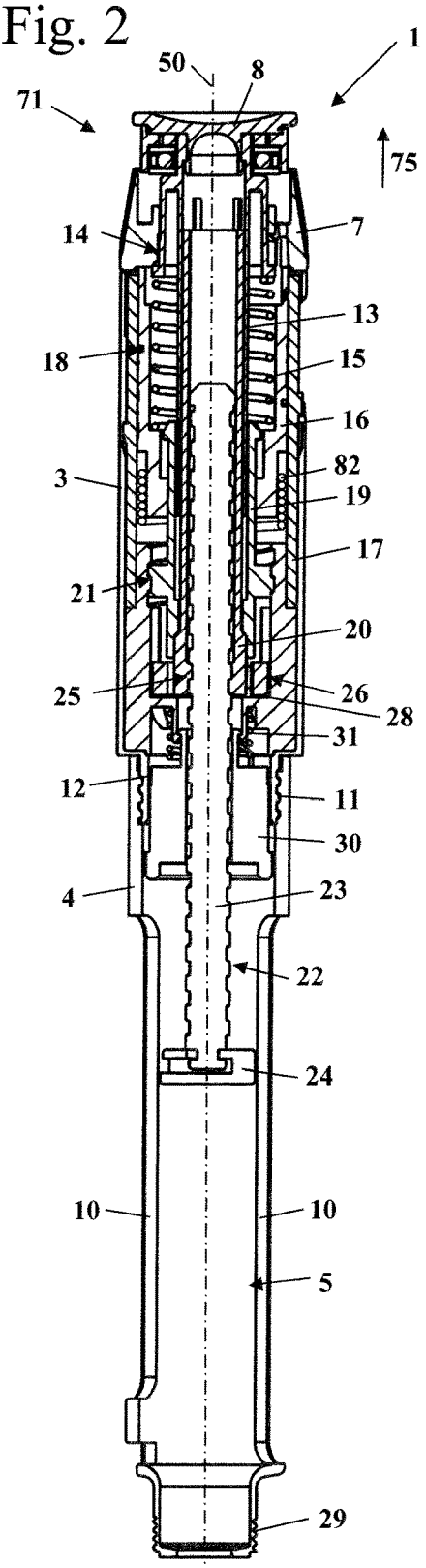

Fig. 6
Fig. 7
Fig. 8
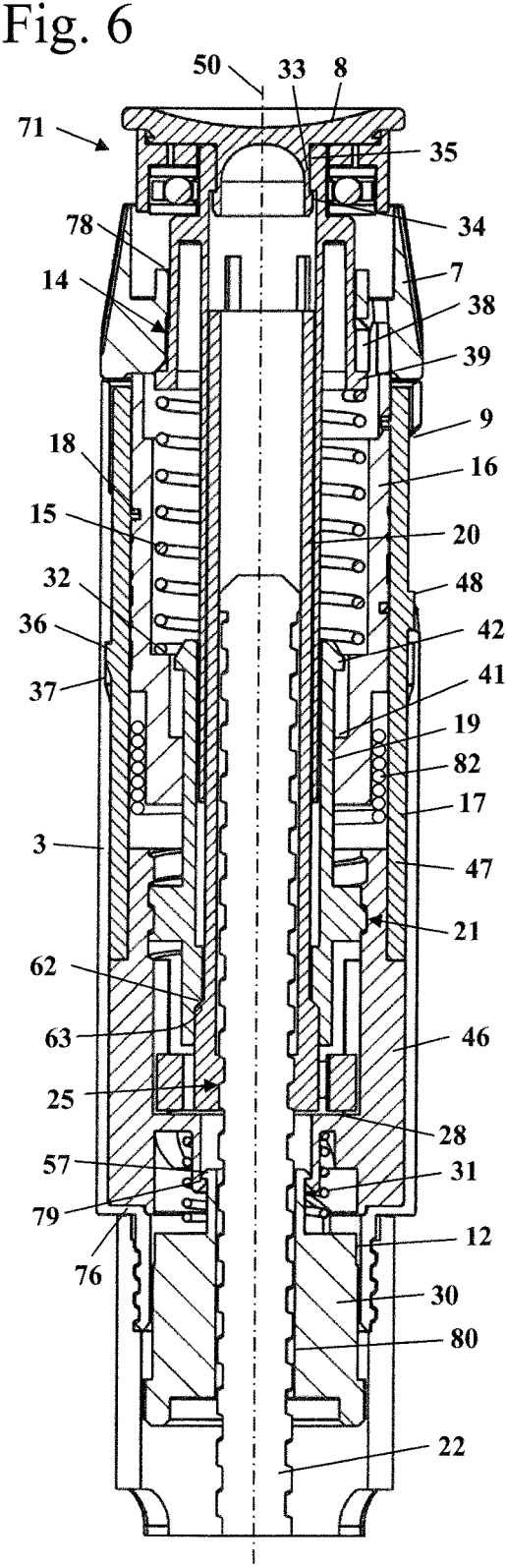
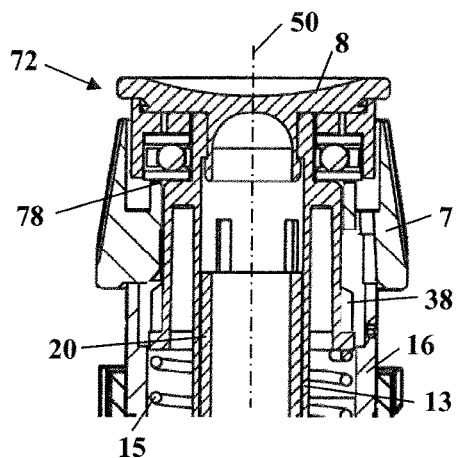
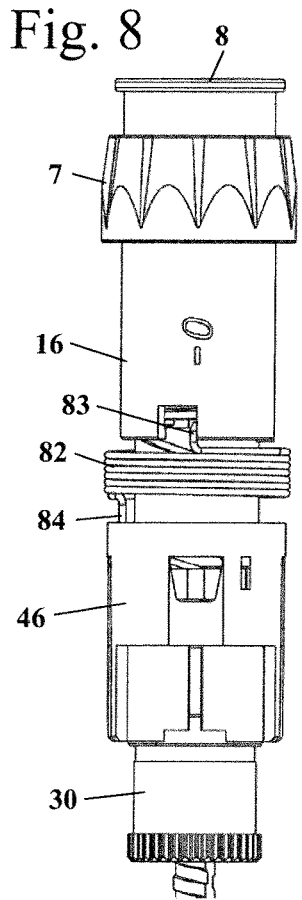

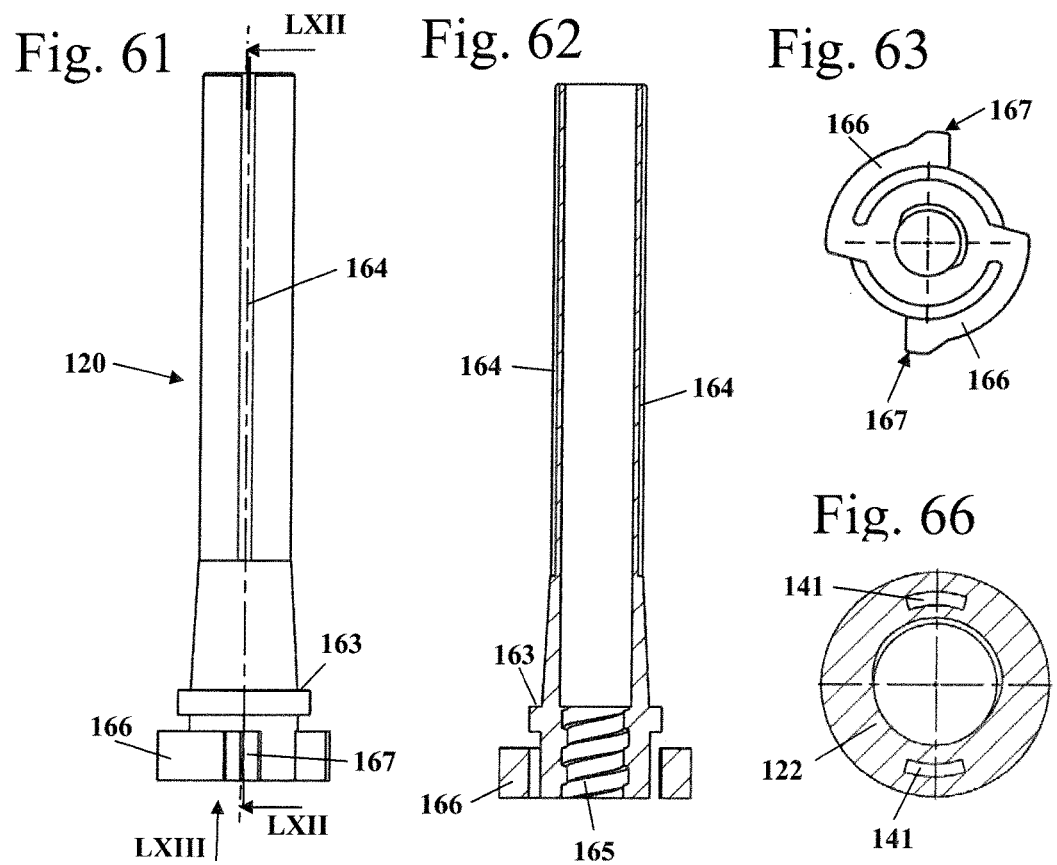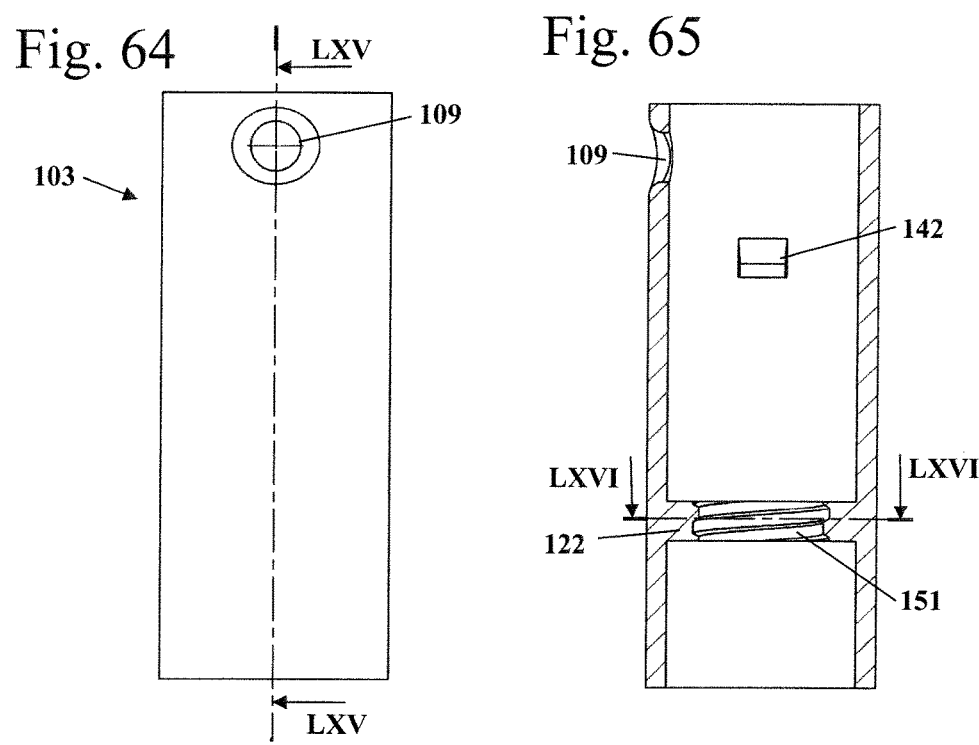

INJECTION DEVICE

CROSS REFERENCE TO RELATED APPLICATIONS

This application is a continuation application of U.S. patent application Ser. No. 14/822,537, filed Aug. 10, 2015, now U.S. Pat. No. 9,694,136, which, in turn, is a continuation application of international patent application PCT/EP2014/000313, filed Feb. 5, 2014, designating the United States and claiming priority from German application 20 2013 001 350.8, filed Feb. 8, 2013, and the entire content of the above applications is incorporated herein by reference.

BACKGROUND OF THE INVENTION

U.S. Pat. No. 8,747,367 discloses an injection device in which, in order to set an injection dose, a dosing member is rotated until the desired dose appears in a window. On account of the rotation, the dosing member moves in the distal direction of the injection device, that is, moves away from an injection needle placed on the injection device. The injection device has a latching device which has a multiplicity of latching positions. As a result, the user can also set the dose by counting a number of palpable or audible latching positions. It is not possible to set intermediate positions between two latching positions. The injection device can have a torsion spring which is without function when setting a dose. When ejecting a set dose from the container, the torsion spring supports the rotation of the setting member and thus the injection.

With the injection device shown in U.S. Pat. No. 8,747,367, a wide variety of quantities of injection fluid can be set. The possible quantities to be set are defined by the latching device. The operating element jumps into the nearest intended position from positions of the operating element which correspond to quantities of injection fluid that are not intended by the manufacturer.

In order that the operating button jumps automatically and reliably from an intermediate position into a latching position, the catch has to be sufficiently strong and the radial latching positions must be located close enough together. However, the strength of latching influences the torque which the user has to apply in order to rotate the operating button and set the dose. The structurally possible spacing of the latching positions is largely defined thereby and can be adapted to the application case only within narrow bounds.

SUMMARY OF THE INVENTION

It is an object of the invention to provide an injection device in which only defined quantities of injection fluid can be ejected from the container and which allows ready adaptation to the desired application case.

This object is achieved by an injection device having an injection device defining a longitudinal center axis and comprising: a housing having a receptacle formed therein for a vessel for holding injection fluid; an operator-manipulated element for setting an injection dose; a dosing member configured to be rotated about the longitudinal center axis relative to the housing when setting the injection dose; the dosing member having a zero position whereat no dose is set and at least one injection position whereat an intended dose of injection fluid is set; a feed part; a latching unit configured to act between the feed part and the housing; the feed part being rotatable about the longitudinal center axis for setting an injection dose; the feed part further being connected to the dosing member in a rotationally fixed manner so as to rotate therewith during the setting of the injection dose; the housing having at least one longitudinal rib; the feed part being configured to move in the direction of the longitudinal center axis with respect to the housing during an ejection of the dose and to be guided on the at least one longitudinal rib; the latching unit having at least one latching element being formed on the longitudinal rib; the latching unit including at least one latching position corresponding to the injection position; the dosing member being positionable in at least one intermediate position whereat no intended dose of injection fluid is set; and, a spring configured to act between the dosing member and the housing so as to return the dosing member, when the operator-manipulated element is unactuated, from the intermediate position to the at least one injection position or the zero position.

The dosing member has at least one injection position in which a dose, intended by the manufacturer, of injection fluid is set. In this case, it is possible for only one injection position to be provided when a medicament is to be administered which is intended to be administered only in a defined dose. However, it is also possible for a plurality of injection positions to be provided, for example when a medicament can be administered in a plurality of different defined doses depending on indication and user. The injection device has a latching device, wherein each injection position of the dosing member is assigned a latching position of the latching device. Depending on the configuration of the latching device, the force exerted on the dosing member by the latching device can be too small to restore the dosing member automatically and securely into the zero position or an injection position from each intermediate position between the zero position and the injection position, or from each intermediate position between two injection positions. In order, in the case of an injection device in which the dosing member can be set in an intermediate position on account of the configuration of the latching device, to avoid the situation in which a user can inject a dose that is not intended, that is, a dose which corresponds to an intermediate position, a spring acts between the dosing member and the housing. As soon as the user releases the operating element in an intermediate position of the dosing member, the dosing member is restored by the spring from the intermediate position into an injection position or the zero position. The injection position and the zero position are intended positions of the dosing member. Advantageously, the dosing member is restored into the next lowest intended position so that accidental injection of too high a dose is avoided.

In conventional injection devices, the setting of the injection dose and the ejection of the injection fluid take place in different operating movements. Between these operating movements, the user usually has to release the operating element. By way of the spring, the dosing member can be restored easily into the next lowest intended position when the user releases the operating element after setting the injection dose and before ejecting the injection fluid from the container.

The dosing member is rotatable about a longitudinal center axis of the injection device in order to set an injection dose. This results in a compact structure and easy handling.

The latching device acts between a feed part and the housing, wherein the feed part is rotatable about the longitudinal center axis of the injection device in order to set an injection dose. The feed part is connected to the dosing member in a rotationally fixed manner during the setting of an injection dose. The feed part moves in the direction of the longitudinal center axis with respect to the housing during the ejection of the dose. As a result, the latching device does not act during the ejection of the injection fluid and no latching steps are audible or palpable to the user. The latching device can furthermore be configured such that it is no longer possible to rotate the feed part back into the next lowest injection position after an injection position has been reached. A simple structure arises in that the feed part is guided on at least one longitudinal rib of the housing. At least one latching element of the latching device is formed on the longitudinal rib. This results in a simple structure. The longitudinal rib simultaneously forms a latching element and the longitudinal guide for the feed part.

Advantageously, the spring is tensioned during the setting of an injection dose. However, provision can also be made for the spring to be largely relaxed in the zero position of the dosing member. The spring acts in particular between the dosing member and the housing. Advantageously, the spring is connected directly to the dosing member and the housing. This results in a favorable installation situation. Particularly advantageously, the spring is a coil spring, wherein a first end of the spring is mounted on the dosing member and a second end of the spring is mounted on the housing. However, provision can also be made for one end of the spring to be fixed to a component held in the housing in a rotationally fixed manner. This can result in a simplified structure of the individual parts of the injection device.

The latching device advantageously provides audible and/or palpable feedback for the user when an injection position is reached. Advantageously, the latching device does not exert any force on the dosing member in intermediate positions of the dosing member. Thus, the restoration of the dosing member into an injection position or the zero position does not take place counter to a force exerted by the latching device. As a result, easy and reliable restoration is achieved, since the restoration force exerted by the spring is not superimposed with a force exerted by the latching device. Since the latching device does not exert any force on the dosing member in intermediate positions of the dosing member, defined latching positions can furthermore be achieved even when there is little available installation space. A simple structure arises when the latching device has at least one resilient catch which cooperates with a latching element.

In the case of a rotatable dosing member, provision is made for the injection positions to be at an angular spacing of at least 30° from one another in the circumferential direction about the longitudinal center axis. At angular spacings of about 30° or more, restoration into intended positions of the dosing member can no longer be reliably ensured simply on account of the geometric configuration of the latching device. The angular spacing between two injection positions is advantageously at least about 45°, in particular at least about 60°. The angular spacing is advantageously selected such that an integer multiple of the angular spacing results in 360°.

The operating element is advantageously configured in a multipart manner and comprises an actuating button and the adjustment sleeve. The adjustment sleeve is connected fixedly to the dosing member. The actuating button is advantageously connected to the feed part via an entrainer, wherein the actuating button is moved in the direction of the longitudinal center axis in the proximal direction of the injection device in order to eject injection fluid from the container. This results in simple, intuitive operation of the injection device. The "proximal direction" denotes in this case the injection direction, that is, in the direction toward a receptacle for the injection needle, or the direction in which the injection fluid is ejected from the container. The "distal direction" denotes the opposite direction, that is, away from the injection needle. The distal end of the injection device is the end that is remote from the injection needle. The term "proximal" denotes that side of the injection device that faces the puncture site during an injection, and "distal" means the side which is remote from the puncture site. A simple configuration of the injection device results when the actuating button is formed in one piece with the entrainer. However, provision can also be made for the entrainer to be connected to the actuating button in an axially fixed manner but so as to be rotatable with respect to the actuating button.

The actuating button is advantageously connected to the adjustment sleeve via a coupling, which establishes a rotationally fixed connection between the entrainer and the adjustment sleeve in a first, distal position of the actuating button, and allows the adjustment sleeve to rotate with respect to the entrainer in a second, proximal position of the actuating button. As a result, it is possible for the feed part to rotate together with the dosing member during the setting of the injection dose and to be guided in the longitudinal direction of the injection device and not to be rotatable with respect to the housing, while the dosing member rotates about the longitudinal center axis of the injection device, during the ejection of the injection fluid out of the container. The rotary movement of the feed part advantageously brings about an axial movement of the feed part by a first travel in the direction of the longitudinal center axis of the injection device via a first threaded connection during the setting of the injection dose. In this case, the feed part is advantageously moved in the distal direction.

A simple structure results, in a first embodiment of the injection device, when the dosing member is mounted in the housing in a rotatable manner and so as to be immovable in the direction of the longitudinal center axis. This is advantageous in particular for injection devices in which the dosing member should be rotated by less than one revolution with respect to the housing in order to set the maximum dose. Advantageously, the injection device has a slide which bears a thread of a second threaded connection. The rotary movement of the slide in this case brings about a movement in the distal direction of the longitudinal center axis by a second travel. The second travel, by which the slide moves, is advantageously at least as large as the first travel, by which the feed part moves.

In order to allow precise setting of an injection dose, provision is advantageously made, in a further embodiment of the injection device, for the dosing member to move in the direction of the longitudinal center axis of the injection device, preferably in the distal direction, during the setting of an injection dose, and for the movements of the feed part and dosing member in the direction of the longitudinal center axis of the injection device to differ from one another. The dosing member is advantageously connected to the housing via a second threaded connection, which brings about the rotary movement of the dosing member into a movement of the dosing member and of the operating element in the direction of the longitudinal center axis of the injection device by a second travel. The second travel, by which the dosing member moves, is in this case greater than the first travel, by which the feed part moves. The dosing member, too, advantageously moves in the distal direction in this case. Advantageously, the injection device has a slide which bears a thread of a third threaded connection. The rotary movement of the slide in this case brings about a movement in the distal direction of the longitudinal center axis by a third travel. The third travel, by which the slide moves, is advantageously at least as large as the first travel, by which the feed part moves. The slide has in particular a driving ledge which cooperates with a driving ledge of the feed part. As a result, the slide can act on the feed part and move the latter in the proximal direction during the ejection of the injection fluid.

BRIEF DESCRIPTION OF THE DRAWINGS

The invention will now be described with reference to the drawings wherein:

FIG. 1 shows a side view of one embodiment of an injection device;

FIG. 2 shows a section along the line II-II in FIG. 1;

FIG. 6 shows an enlarged illustration of the distal housing part of the injection device from FIG. 2;

FIG. 7 shows a sectional illustration of a detail of the injection device from FIG. 5 in the region of the operating element after the actuating button has been pressed;

FIG. 8 shows a side view of the injection device with the housing removed;

FIG. 61 shows a side view of the feed part in FIGS. 59 and 60;

FIG. 62 shows a section along the line LXII-LXII in FIG. 61;

FIG. 63 shows a side view in the direction of the arrow LXIII in FIG. 61;

FIG. 64 shows a side view of the upper housing part of the injection device from FIG. 29;

FIG. 65 shows a section along the line LXV-LXV in FIG. 64;

FIG. 66 shows a section along the line LXVI-LXVI in FIG. 65;

DESCRIPTION OF THE PREFERRED EMBODIMENTS OF THE INVENTION

Figure 3:
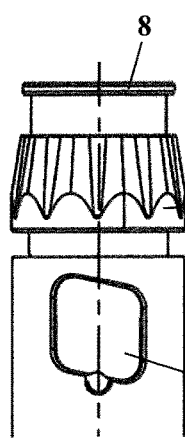
FIG. 3 shows a portion of the injection device from FIG. 1 following the setting of a non-intended quantity of injection fluid.

The injection device 1 shown in FIG. 1 has a housing 2, which comprises an upper, distal housing part 3 and a holder 4 arranged on the proximal side of the upper housing part 3. At its proximal end, the holder 4 has an external thread 29 on which an injection needle 81, schematically shown in FIG. 1, can be screwed. Formed in the holder 4 is a receptacle 5, shown in FIG. 2, for a container or vessel containing injection fluid. The container containing injection fluid is not shown in the figures for the first embodiment. As FIG. 1 shows, the holder 4 has at least one cutout 10, through which the container containing injection fluid is visible. As a result, the user can easily identify whether injection fluid is still present in the container. As FIG. 2 shows, two cutouts 10 that are arranged opposite one another are provided on the holder 4.

As FIG. 1 shows, an operating element 6, which has an adjustment sleeve 7 and an actuating button 8 arranged on the distal side of the adjustment sleeve 7, is arranged at the distal end of the housing part 3. Adjacently to the adjustment sleeve 7, the housing part 3 has a window 9 through which a scale applied to a dosing member 16 is discernible. The dosing member 16 is arranged in the housing part 3. In FIG. 1, the scale shows a "0", which signals to the user that a quantity has not been set. The dosing member 16 is in a zero position 85, in which no dose is set.

FIG. 2 shows the structure of the injection device 1 in detail. The injection device 1 has an entrainer 13, which is configured in a substantially sleeve-like manner and is fixedly connected axially to the actuating button 8 of the operating element 6. The term "axial" relates in each case to the direction of a longitudinal center axis 50 of the injection device 1, here. The actuating button 8 is connected to the entrainer 13 via a snap connection which allows the actuating button 8 to rotate with respect to the entrainer 13. The entrainer 13 is connected to the adjustment sleeve 7 of the operating element 6 via a coupling 14. In the first, distal position 71, shown in FIG. 2, of the actuating button 8, the coupling 14 is closed. The adjustment sleeve 7 of the operating element 6 is connected to the entrainer 13 in a rotationally fixed manner. The adjustment sleeve 7 is fixedly connected to the dosing member 16, which is also referred to as setting member or scale tube. The entrainer 13 is connected to a feed part 20 in a rotationally fixed manner, the feed part 20 being connected to a piston rod 23 of a dosing piston 22 by a first threaded connection 25. The piston rod 23 bears at its proximal end a piston disk 24, which serves for abutment against a stopper of the container containing injection fluid, and via which the injection fluid is ejected from the container.

The piston rod 23 is held in a rotationally fixed manner in a piston rod ring 30. The piston rod ring 30 is arranged in an axially movable manner in the injection device 1. In the position shown in FIG. 2, when no container has been inserted into the receptacle 5, the piston rod ring 30 is pushed into its proximal position by a compression spring 31. In this position, the piston rod ring 30 is rotatable with respect to the housing part 3. If a container is inserted into the receptacle 5 and the holder is connected to the housing part 3 by way of a fastening thread 11, then the container pushes the piston rod ring 30 in the distal direction. The injection device 1 has an internal tube 17, which is part of the housing 2 and is connected to the housing part in a rotationally fixed manner and fixedly in the axial direction. At its distal end, the piston rod ring 30 has a contour which is coordinated with a contour of the internal tube 17. In its distal position, the piston rod ring 30 is connected in a rotationally fixed manner to the internal tube 17, and thus also in a rotationally fixed manner to the housing part 3, via the contours. With a container inserted into the receptacle 5, the piston rod 23 is held in the housing part 3 in a rotationally fixed manner thereby. As a result of the rotationally fixed connection of the piston rod 23 and housing part 3, a rotation of the feed part 20 brings about a movement of the feed part 20 in the distal direction, that is, in the direction of the arrow 75 in FIG. 2. Formed between the feed part 20 and the internal tube 17 is a latching connection device 26 which defines latching positions of the feed part 20. In the position, shown in FIG. 2, of the feed part 20, the feed part 20 bears against a stop 28 formed on the internal tube 17, the stop defining the position of the feed part 20 in the axial direction.

The dosing member 16 is connected to the internal tube 17 via a second threaded connection 18. The internal tube 17 is fixedly connected to the housing part 3. The internal tube 17 could also be formed in one piece with the housing part 3, but as a result, the production of the injection device 1 becomes very complicated. The dosing member 16 is connected in a rotationally fixed and axially movable manner to a slide 19, which projects into the interior of the dosing member 16. The slide 19 is connected to the internal tube 17 via a third threaded connection 21. Between the entrainer 13 and the dosing member 16 there acts a compression spring 15, which presses the actuating button 8 into its first position 71. Between the dosing member 16 and the housing 3 there acts a spring 82. The spring 82 is advantageously configured as a torsion spring. In the embodiment, the spring 82 is a helical tension spring, which is both elongated and rotated about the longitudinal center axis 50 of the injection device 1 during the setting of an injection dose.

In order to set the quantity of injection fluid to be ejected, the user rotates the operating element 6 until the desired dose appears in the window 9. In the process, the adjustment sleeve 7 rotates. The dosing member 16, which is connected in a rotationally fixed manner to the adjustment sleeve 7, rotates as a result with respect to the upper housing part 3 and the internal tube 17. On account of its rotary movement, the dosing member 16 is pushed in the distal direction, that is, in the direction of the arrow 75, via the second threaded connection 18. The operating element 6 and the entrainer 13, which is connected in an axially fixed manner to the actuating button 8 of the operating element 6, move with the dosing member 16. The operating element 6, the entrainer 13 and the dosing member 16 move together in the distal direction and in the process rotate about the longitudinal center axis 50 on account of the second threaded connection 18.

Via the rotationally fixed connection between the entrainer 13 and feed part 20, the feed part 20 also rotates with respect to the upper housing part 3. Via the first threaded connection 25, the feed part 20 also moves in the distal direction. The slide 19 likewise moves in the distal direction, since the slide 19 is connected in a rotationally fixed manner to the dosing member 16. The slide 19 and the feed part 20 also move with a combined rotary and longitudinal movement, wherein the distances that the slide 19 and the feed part 20 cover in the direction of the longitudinal center axis 50 are fixed via the first threaded connection 25 and via the third threaded connection 21, respectively. Provision can also be made for the slide 19 to be connected to the dosing member 16 via a third threaded connection and to be connected in a rotationally fixed manner to the housing part 3.

FIG. 3 shows the injection device 1 following the setting of a dose of injection fluid that is not intended by the manufacturer. The dosing member 16 is located in an intermediate position 74 which will be explained in more detail in the following text.

Figure 4:
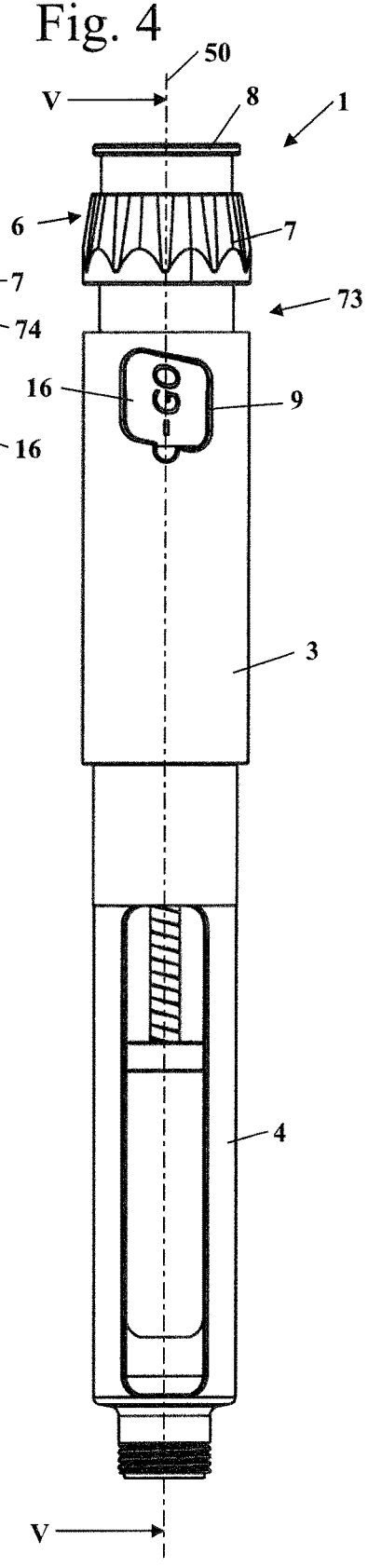
FIG. 4 shows the injection device from FIG. 1 following the setting of an intended quantity, to be ejected, of injection fluid.
Figure 5:
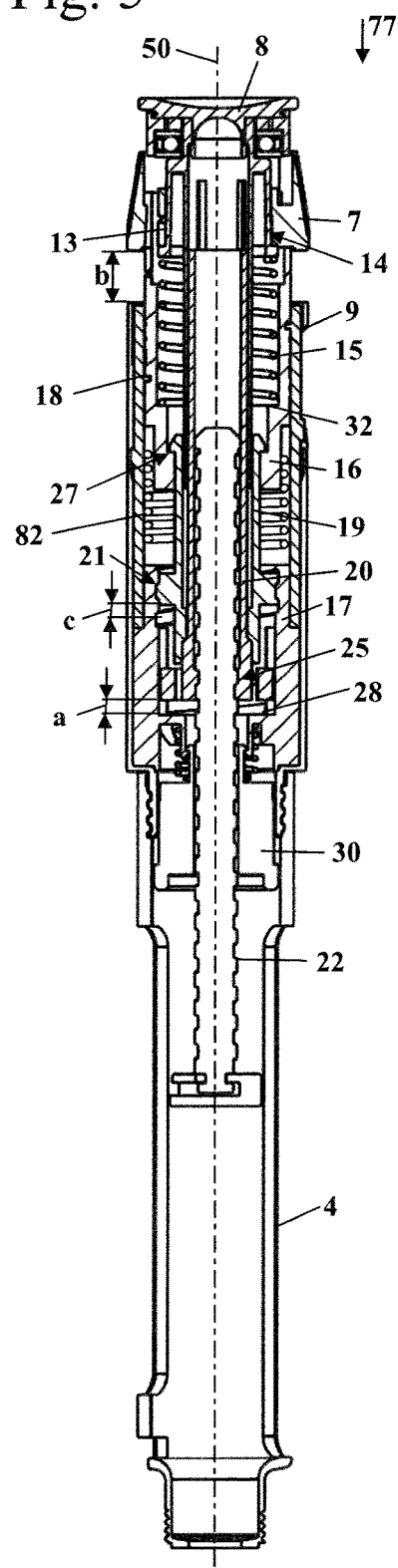
FIG. 5 shows a section along the line V-V in FIG. 4.

FIGS. 4 and 5 show the injection device 1 following the setting of an intended quantity of injection fluid to be ejected. The feed part 20 has moved by a first travel (a) in the distal direction. Following the setting of the quantity of injection fluid to be ejected, the end side of the feed part 20 has moved away from the stop 28 by the first travel (a). The operating element 6 having the adjustment sleeve 7 and the actuating button 8 has moved in the distal direction by a second travel (b). The second travel (b) is measured in the embodiment between the proximal end side of the adjustment sleeve 7 and the distal end side of the housing part 3. The second travel (b) is much greater than the first travel (a). In the embodiment, the second travel (b) is a multiple of the travel (a), for example about three times the travel (a). The different travels (a) and (b) result from different pitches of the first threaded connection 25 and of the second threaded connection 18. The dosing member 16 has also moved in the distal direction by the second travel (b). The slide 19 has moved in the distal direction by a third travel (c). The travel (c) can be the same size as the travel (a). However, provision can also be made for the travel (c) to be greater than the travel (a). The third travel (c) is indicated in FIG. 5 at the proximal end side of that portion of the slide 19 that bears the thread, specifically opposite the position of the end side in FIG. 2. During the setting of the quantity of injection fluid to be ejected, the spring 82 was tensioned. In the process, the spring 82 was elongated by the second travel (b). At the same time, the ends 83 and 84 of the spring 82 that are shown in FIG. 8 were rotated about the longitudinal center axis 50 with respect to the housing 2 on account of the rotation of the dosing member 16.

The maximum quantity of injection fluid to be set is defined by the distance by which the actuating button 8 and the dosing member 16 can move in the distal direction. This distance is limited by a stop 27 (FIG. 5) formed between the dosing member 16 and the slide 19. As FIG. 4 shows, the dosing member 16 has, at its proximal end, an inwardly directed ledge 41. A latching rim 42 on the slide 19 engages behind this ledge 41 in the axial direction. With the latching rim 42, the ledge 41 forms the stop 27. As soon as the latching rim 42 bears against the ledge 41, the maximum settable quantity of injection fluid has been achieved. The spacing between the ledge 41 and the latching rim 42 in the state, shown in FIGS. 1 and 2, of the injection device 1 corresponds to the second travel (b) minus the first travel (a).

As FIG. 6 shows, the first housing part 3 has a latching depression 37 which is formed in a circumferential manner in the embodiment. A catch 36 that projects radially outwards and is formed on the internal tube 17 projects into the latching depression 37, the catch 36 securing the internal tube 17 in the housing part 3 in the direction of the longitudinal center axis 50 of the injection device 1. At its proximal end, the internal tube 17 bears against a shoulder 76 of the housing part 3. In order to secure the rotary position, the internal tube 17 has an outwardly projecting peg 48 which latches at the housing part 3 adjacently to the window 9.

FIG. 6 also shows the support of the compression spring 15. The compression spring 15 is supported by way of its proximal end against a shoulder 32 of the dosing member 16 and by way of its distal end against a rim 39 formed on the entrainer 13. The rim 39 projects outwardly from a sleeve-like portion of the entrainer 13. Adjacently to the rim 39, an external toothing 38 is arranged on the entrainer 13 at the distal side of the rim 39. The external toothing 38 cooperates with an internal toothing (not shown) on the adjustment sleeve 7 and forms the coupling 14 with the latter. In the non-actuated position, shown in FIG. 6, of the actuating button 8, the coupling 14 is closed and establishes a rotationally fixed connection between the entrainer 13 and an adjustment sleeve 7. The compression spring 15 pushes the entrainer 13 in the direction of the closed position of the coupling 14. As a result, the actuating button 8 is pressed in the direction of its distal position 71.

After the dose to be injected has been set, an injection can be initiated. To this end, the actuating button 8 is pressed in the direction of the arrow 77 in FIG. 5, that is, in the proximal direction. As a result, the actuating button 8 moves into the adjustment sleeve 7, counter to the force of the compression spring 15, in the direction of the longitudinal center axis 50, until the actuating button 8 bears against a stop 78 on the adjustment sleeve 7. FIG. 7 shows the actuating button 8 in its second, proximal position 72. In this position, the external toothing 38 of the entrainer 13 has moved out of the region of the adjustment sleeve 7. As a result, the adjustment sleeve 7 is rotatable with respect to the entrainer 13 and the actuating button 8. The coupling 14 is open. When the actuating button 8 continues to be pressed in the direction of the arrow 77 in FIG. 5, the dosing member 16 is pushed into the internal tube 17 and in the process moves in the proximal direction. In this case, the dosing member 16 rotates on account of the second threaded connection 18. On account of the rotation of the dosing member 16, the slide 19 is also rotated and as a result moves in the proximal direction. The rotation of the dosing member 16 with respect to the housing 3 is supported by the spring 82. The slide 19 has a driving ledge 62, which bears against a driving ledge 63 of the feed part 20. Via the driving ledges 62 and 63, the slide 19 presses, during its movement in the proximal direction, against the feed part 20 and moves the latter likewise in the proximal direction. The feed part 20 is connected in a rotationally fixed manner to the entrainer 13, which is connected in an axially fixed manner to the nonrotating actuating button 8. The rotation of the feed part 20 is prevented by the latching device 26, which has been positioned in a latching position during the setting of the dose. As a result, the rotating slide 19 cannot rotate the feed part 20 along with it. Since the feed part 20 does not rotate and the dosing piston 22 is also connected in a rotationally fixed manner to the housing part 3 via the piston rod ring 30, the feed part 20 and the dosing piston 22 are connected fixedly together and move together in the proximal direction, until the feed part 20 bears against the stop 28 and the set quantity of injection fluid has been ejected in its entirety from the container.

The injection device 1 is intended to inject defined doses of injection fluid. The dosing member 16 has at least one injection position 73, shown in FIG. 4, in which a structurally defined, intended quantity of injection fluid is set. The latching device 26 latches in injection positions 73. The dosing member 16 can also be positioned in at least one intermediate position 74, which is shown in FIG. 3. In an intermediate position 74 of the dosing member 16, a non-intended quantity of injection fluid is set. The latching device 26 does not latch in intermediate positions 74 of the dosing member 16. If non-intended doses of injection fluid are set, the dosing member 16 is restored into the next lowest injection position 73 or the zero position 85 by the spring 82 as soon as the user releases the adjustment sleeve is 7.

As FIG. 6 shows, the internal tube 17 of the housing 7 is constructed from a proximal part 46 and a distal part 47, which are connected fixedly together. The internal tube 17 can also be produced in one piece. However, this makes the internal tube 17 much more complicated to produce. In order to further simplify production, it can be advantageous to form the internal tube 17 from more than two individual parts. As FIG. 8 shows, the spring 82 acts between the proximal part 46 of the internal tube 17 and the dosing member 16. In this case, a first end 83 of the spring 82 is fixed to the dosing member 16 and a second end 84 is fixed to the proximal part 46 of the internal tube 17. The ends 83 and 84 are in this case mounted advantageously in corresponding recesses in the dosing member 16 and proximal part 46.

Figure 9:
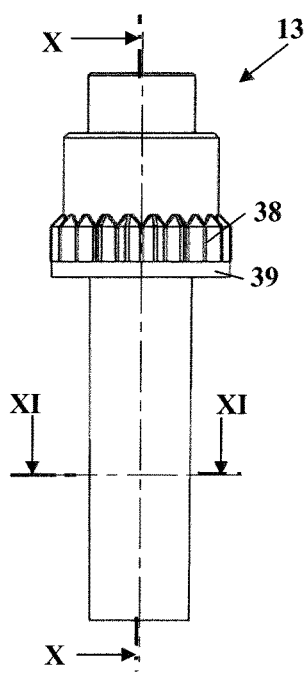
FIG. 9 shows a side view of the entrainer of the injection device.
Figure 10:
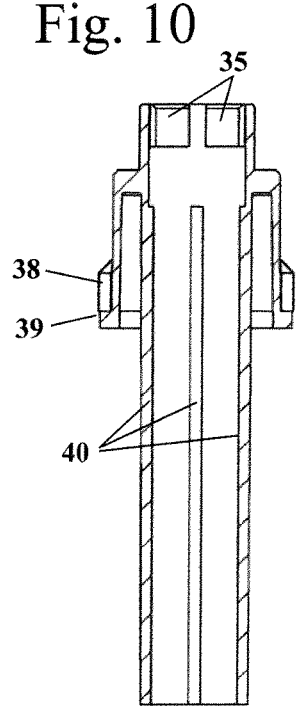
FIG. 10 shows a section along the line X-X in FIG. 9.
Figure 11:
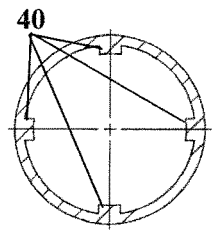
FIG. 11 shows a section along the line XI-XI in FIG. 9.

FIGS. 9 to 27 show the components of the injection device 1 in detail. FIGS. 9 to 11 show the entrainer 13. For connection to the actuating button 8, the entrainer 13 has, at its distal end, internal latching elevations 35, which engage behind a latching rim 34, shown in FIG. 6, that is formed on a connecting piece 33 of the actuating button 8, and as a result connect the actuating button 8 to the entrainer 13 in the axial direction. In the embodiment, the sleeve-like entrainer 13 has on its inner circumference four guiding ribs 40 that extend in the axial direction. The guide ribs 40 match longitudinal grooves 64, shown in FIG. 22, in the feed part 20 and engage therein. The guide ribs 40 establish, with the longitudinal grooves 64, the rotationally fixed connection between the entrainer 13 and the feed part 20. The guide ribs 40 are freely movable in the longitudinal grooves 64 in the direction of the longitudinal center axis 50 of the injection device 1.

Figure 12:
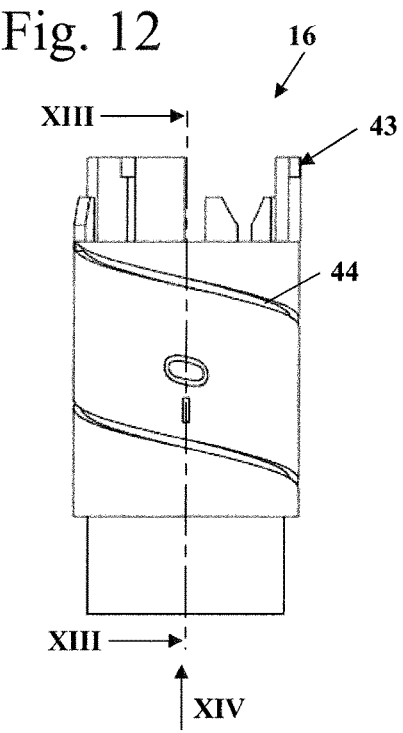
FIG. 12 shows a side view of the dosing member of the injection device.
Figure 13:
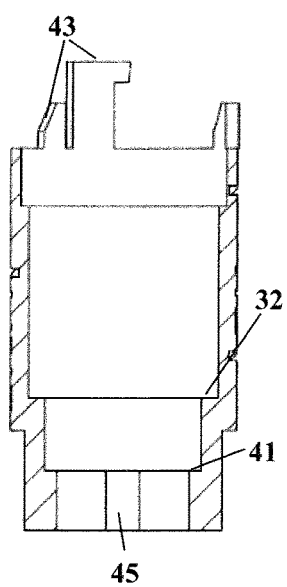
FIG. 13 shows a section along the line XIII-XIII in FIG. 12.
Figure 14:
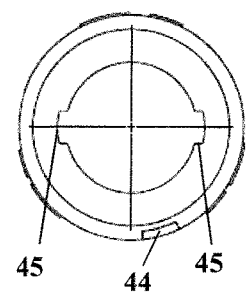
FIG. 14 shows a side view of the dosing member in the direction of the arrow XIV in FIG. 12.
Figure 19:
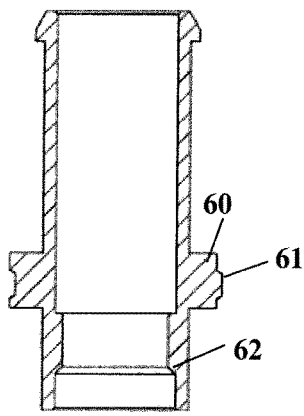
FIG. 19 shows a section along the line XIX-XIX in FIG. 18.
Figure 21:
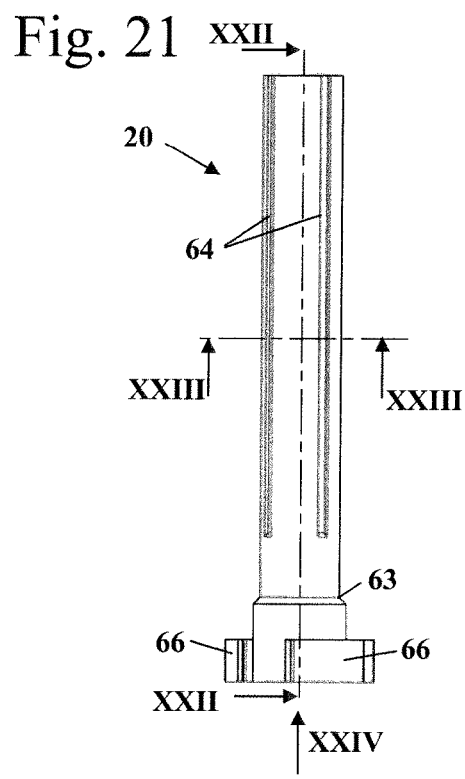
FIG. 21 shows a side view of the feed part of the injection device.

FIGS. 12 to 14 show the dosing member 16, which is also referred to as scale tube or setting member. The dosing member 16 is formed in a sleeve-like manner and has an external thread 44 on its outer circumference. The external thread 44 is configured as a groove extending helically around the outer circumference of the dosing member 16. As its distal end, the dosing member 16 bears a connecting contour 43 which is formed from hook- and ramp-like elements, which establish a rotationally fixed connection to the adjustment sleeve 7. As FIGS. 13 and 14 show, the dosing member 16 has, at its proximal end, two guide grooves 45 which extend parallel to the longitudinal center axis 50. The guide grooves 45 are arranged opposite one another and cooperate with longitudinal ribs 59 on the slide 19, which are shown in FIGS. 19 and 21. Via the longitudinal ribs 59, which are guided in the longitudinal grooves 45, a rotationally fixed connection is produced between the dosing member 16 and the slide 19. The longitudinal ribs 59 are freely movable in the guide grooves 45 in the direction of the longitudinal center axis 50, such that the slide 19 is movable with respect to the dosing member 16 in the direction of the longitudinal center axis 50.

Figure 15:
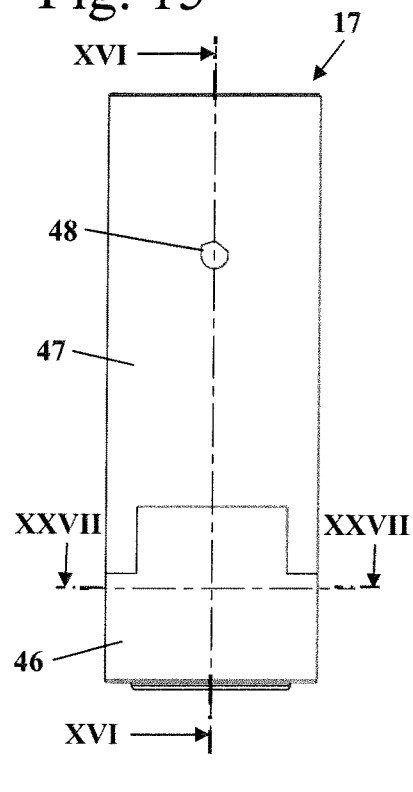
FIG. 15 shows a side view of an internal tube of the injection device.
Figure 16:
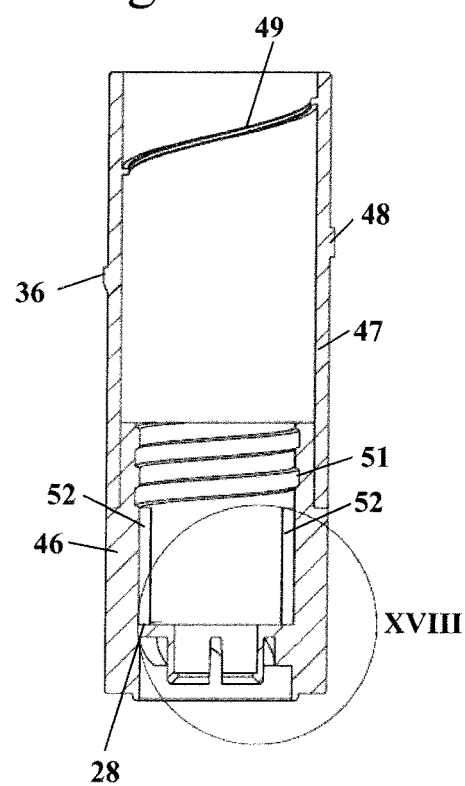
FIG. 16 shows a section along the line XVI-XVI in FIG. 15.
Figure 17:
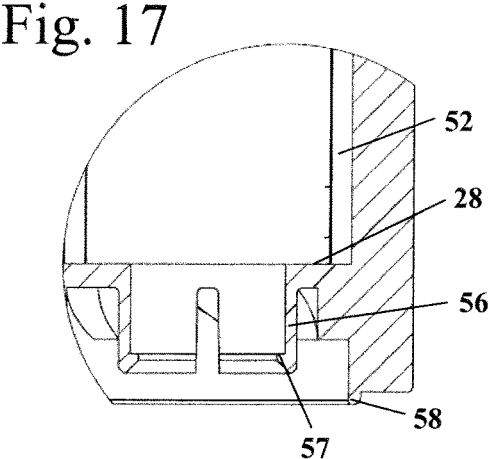
FIG. 17 shows an enlarged illustration of the detail XVII in FIG. 16.
Figure 27:
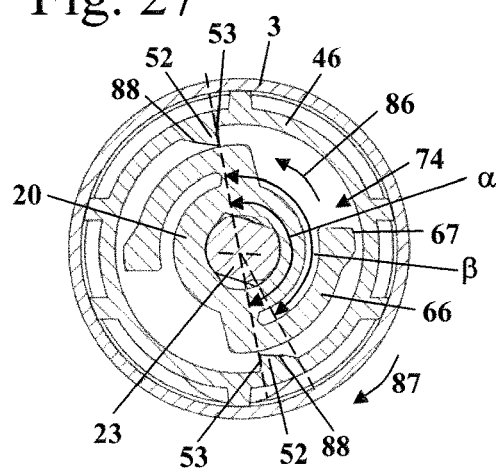
FIG. 27 shows a section through the internal tube at the level of the line XXVII-XXVII in FIG. 15 with the feed part, arranged therein, in the locked position of the operating element.
Figure 28:
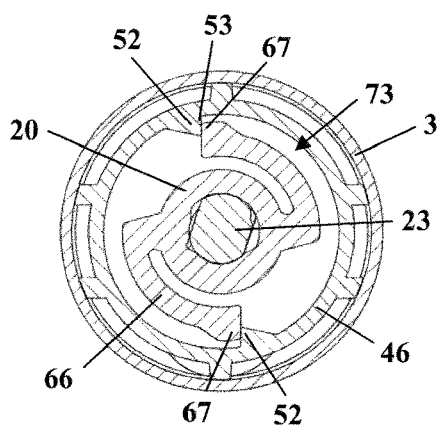
FIG. 28 shows a sectional illustration corresponding to FIG. 27 with the feed part in the injection position of the operating element.

FIGS. 15 to 17 show the internal tube 17. The internal tube 17 is embodied in two parts and includes the proximal part 46 and the distal part 47, which are connected fixedly together. Arranged in the distal part 47 of the internal tube 17 is an internal thread 49, which is formed from a rib extending spirally around the inner circumference. The internal thread 49 is formed by a single thread. Provision can be made to form the internal thread 49 only from one or more sections of a thread. The internal thread 49 cooperates with an external thread 44 of the dosing member 16 and brings about an axial movement of the dosing member 16 upon rotation of the dosing member 16. Formed in the proximal part 46 of the internal tube 17 is an internal thread 51, which cooperates with an external thread 61, shown in FIG. 18, of the slide 19. With the external thread 61, the internal thread 51 forms the third threaded connection 21. Longitudinal ribs 52 follow on the proximal side of the internal thread 51. As FIG. 27 shows, a total of two longitudinal ribs 52 are provided in the embodiment, the longitudinal ribs 52 being arranged more or less opposite one another. With the two mutually opposite catches 67 of the feed part 20, the longitudinal ribs 52 define the latching positions of the latching device and thus the injection positions 73. In the embodiment, the two injection positions 73 are at an angular spacing α of 180°. The angular spacing α is advantageously at least about 30°, in particular at least about 45°, particularly advantageously at least 60°. In the circumferential direction, the longitudinal ribs 52 are at an angular spacing β, shown in FIG. 27, which is somewhat less than 180° in the embodiment, for example about 160° to 175°. The angular spacing β corresponds to the angular range in which the dosing member 16 can be positioned in intermediate positions 74 between two injection positions 73 or an injection position 73 and a zero position 85. Advantageously, the latching device 26 does not exert any force on the feed part 20 and thus on the dosing member 16 in this angular range. A different number of longitudinal ribs 52 and/or catches 67 may also be advantageous. For example, provision can be made of four longitudinal ribs 52 and two catches 67, which are arranged such that an angular spacing α of 90° is produced between the injection positions 73.

In the embodiment, the longitudinal ribs 52 and the catches 67 are configured such that it is not possible to rotate the operating element 6 back out of the latching position into a position which is assigned to a smaller quantity of injection fluid. However, provision can also be made for the shape of the longitudinal ribs 52 and catches 67 to allow the operating element 6 to be rotated back, for example by a symmetrical configuration in the circumferential direction.

As FIG. 17 shows, a centering rim 58 projects in the proximal direction of the proximal end of the internal tube 17. The centering rim 58 projects into a proximal opening in the housing part 3 and ensures a firm fit of the internal tube 17 in the housing part 3. On the proximal side of the internal tube 17, holding connecting pieces 56 furthermore project in the proximal direction, latching rims 57 that project radially inward being integrally formed on the proximal end of the holding connecting pieces 56. The latching rims 57 cooperate with latching rims 79 of the piston rod ring 30, which is shown in FIG. 5. The latching rim 79 provides, with the latching rim 57, axial securing for the piston rod ring 30. As FIG. 5 shows, the second compression spring 31 pushes the piston rod ring 30 into its proximal position until the latching rim 79 bears against the latching rim 57. In this position, the user can rotate the housing part 3 with respect to the piston rod ring 30 in order to move the dosing piston 22 in the distal direction. This is provided for changing a container for injection fluid.

Figure 18:
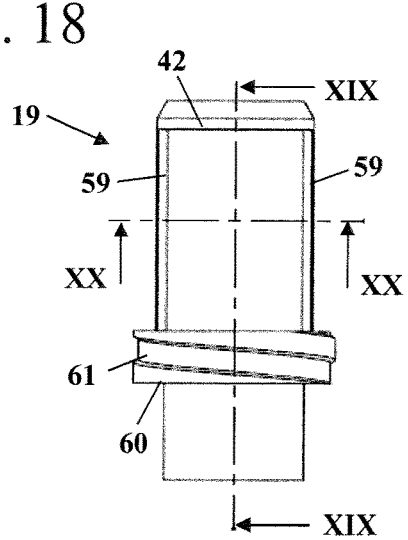
FIG. 18 shows a side view of the slide of the injection device.
Figure 20:
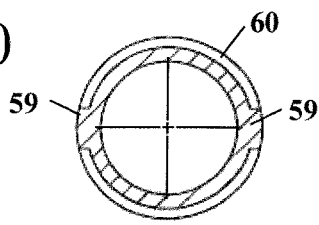
FIG. 20 shows a section along the line XX-XX in FIG. 18.

FIGS. 18 to 20 show the slide 19 in detail. At its distal end, the slide 19 has the latching rim 42. As FIGS. 18 and 19 show, the external thread 61 is formed on an annular rib 60 which projects radially outward. The slide 19 is also formed in a substantially sleeve-like manner.

Figure 22:
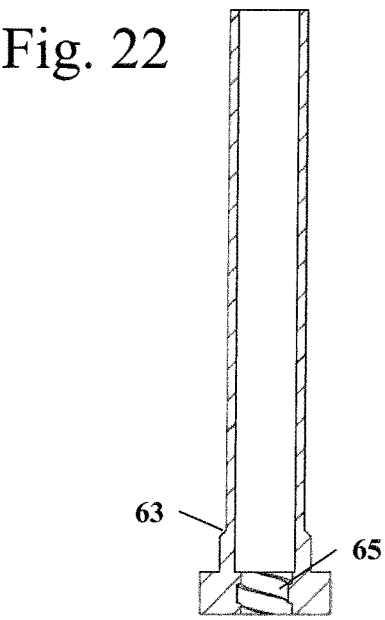
FIG. 22 shows a section along the line XXII-XXII in FIG. 21.
Figure 23:
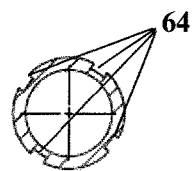
FIG. 23 shows a section along the line XXIII-XXIII in FIG. 21.
Figure 24:
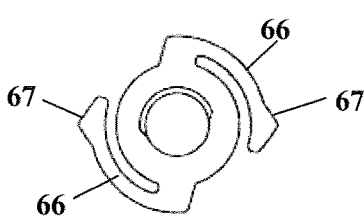
FIG. 24 shows a side view of the feed part in the direction of the arrow XXIV in FIG. 21.

FIGS. 21 to 24 show the feed part 20. At its proximal end, the feed part 20 has two latching arms 66, which are shown in FIG. 24. At their free ends, the latching arms 66 each have a catch 67, which is directed radially outward. The latching arms 66 extend approximately in the circumferential direction and are configured to be resilient in the radially outward direction. FIG. 22 shows an internal thread 65 which is formed at the proximal end of the feed part 20 and which cooperates with the dosing piston 22. The internal thread 65 and the latching arms 66 are arranged in the same longitudinal portion of the feed part 20.

Figure 25:
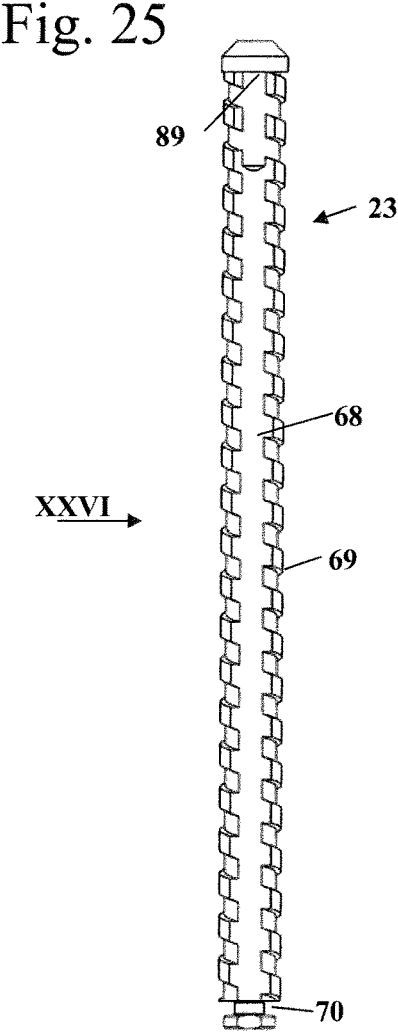
FIG. 25 shows a side view of the piston rod of the dosing piston of the injection device.
Figure 26:
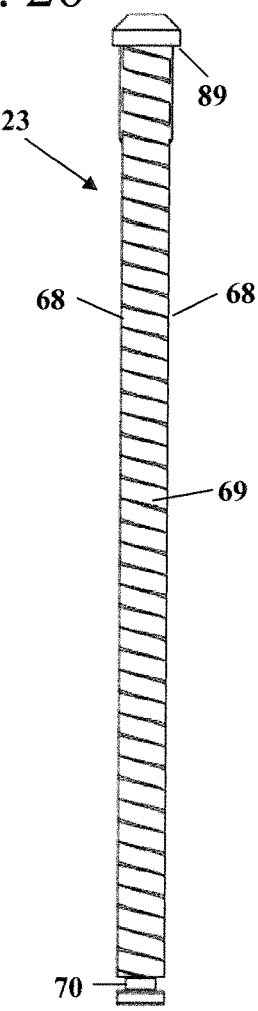
FIG. 26 shows a side view in the direction of the arrow XXVI in FIG. 25.

As FIGS. 25 and 26 show, the piston rod 23 has an external thread 69 which cooperates with the internal thread 65 of the feed part 20 and forms the first threaded connection 25 therewith. On its opposite longitudinal sides, the piston rod 23 has flattened portions 68 which cooperate with corresponding flattened portions of an opening 80, shown in FIG. 5, in the piston rod ring 30, in order to secure the rotary position of the piston rod 23. At its proximal end, the piston rod 23 has a fastening groove 70, by way of which the piston disk 24 is held. At its distal end, the piston rod 23 has a stop 89. At the distal end of the piston rod 23, the external thread 69 ends in a contour which has, in the embodiment, a round cross section with a diameter which is greater than the outside diameter of the external thread 69. The proximal face of this contour forms the stop 89 with respect to the internal thread 65 of the feed part 20. At the stop 89, the piston rod 23 has, in the embodiment, a round cross section, the outside diameter of which corresponds more or less to the greatest outside diameter of the piston rod 23. As a result, the stop 89 cannot be screwed into the internal thread 65 of the feed part 20. However, some other configuration of the stop 89, which prevents screwing into the internal thread 65, can be advantageous. The stop 89 is arranged such that the stop 89 butts against the feed part 20 when the quantity of injection fluid still present in the container is set. As a result, the user cannot set a dose which is greater than the remaining quantity of injection fluid present in the container.

FIG. 27 shows the arrangement of the feed part 20 in an intermediate position 74 of the operating element 6, dosing member 16 and feed part 20. The catches 67 are spaced apart from the longitudinal ribs 52. The spring 82 (FIG. 8) acts on the dosing member 16 in the direction of the zero position 85 of the dosing member 16. Via the coupling 14, which is closed during the setting of the injection dose, and the entrainer 13, the spring 82 also acts on the feed part 20. The feed part 20 is loaded, in the direction of the arrow 86 shown in FIG. 27, in the direction of the previous latching position of the catches 67. As soon as the user releases the adjustment sleeve 7, for example in order to press the operating button 8 and inject a dose, the dosing member 16 and the feed part 20 are restored into the previous intended position, which is assigned to the next lowest intended dose or no dose of injection fluid, on account of the force of the spring 82. In the process, the feed part 20 rotates in the direction of the arrow 86. Intended positions are in this case injection positions 73 or the zero position 85. Since it is not possible to set a non-intended quantity of injection fluid, the ejection of a non-intended quantity of injection fluid is prevented.

If the operating element 6 and also the feed part 20 are rotated further, the catches 67, after overcoming the longitudinal ribs 52, which form the latching device 26 with the catches 67, pass behind the longitudinal ribs 52 in the direction of rotation 87. The direction of rotation 87 is the direction of rotation in which the feed part 20 and the dosing member 16 rotate during the setting of the dose of injection fluid. The longitudinal ribs form, at their sides that are located at the front in the direction of the arrow 86, latching elements 53 at which the catches 67 latch. If the catches 67 bear against the latching elements 53 of the longitudinal ribs 52, the latching device 26 is latched, and the arrangement is in an intended injection position 73. Further automatic movement of the feed part 20 in the direction of the arrow 86 on account of the force of the spring 82 is avoided by the abutment of the catches 67 against the latching elements 53. The user can press the operating button 8 and inject the set dose. The ejection of the set quantity of injection fluid is supported by the spring 82. At the longitudinal ribs 52, the catches 67 are guided in this case parallel to the longitudinal center axis 50 of the injection device 1. As a result, the longitudinal ribs 52 ensure that the feed part 20 cannot rotate about the longitudinal center axis 50 during the injection of a dose and as a result reduce the quantity of injection fluid to be ejected.

At their sides that are located at the front in the direction of rotation 87, the longitudinal ribs 52 each have a slope 88, the slopes 88 deflecting the catches 67 radially inward and thus making it easier to overcome the longitudinal ribs 52. The slopes 88 exert a force counter to the direction of rotation 87 on the catches 67 and thus on the feed part 20 and the dosing member 16. In positions of the dosing member 16 in which the catches bear against the slopes 88, the feed part 20 is restored counter to the direction of rotation 87, on account of the force exerted by the latching device 26, until the catches 67 no longer bear against the slopes 88 when the user does not exert an opposing force on the feed part 20. At the angular spacing β between the longitudinal ribs 52, the catches 67 are at a spacing from the proximal part 46 of the internal tube 17 and are not in contact with the proximal part 46. Advantageously, the inner circumference of the proximal part 46 extends in this region in a circular arc about the longitudinal center axis 50. In this region, the latching device 26 does not exert any force on the feed part 20 or the dosing member 16. The restoration of the feed part 20 and of the dosing member 16 into an injection position 73 or the zero position 85 takes place in this region exclusively on account of the force of the spring 82. The embodiment shows an injection device 1 in which only a single defined quantity of injection fluid can be ejected from the container. This quantity is reached when the operating element has been rotated through 180°. However, provision can also be made for a plurality of injection positions 73, which are assigned to different quantities of injection fluid, to be possible.

Figure 29:
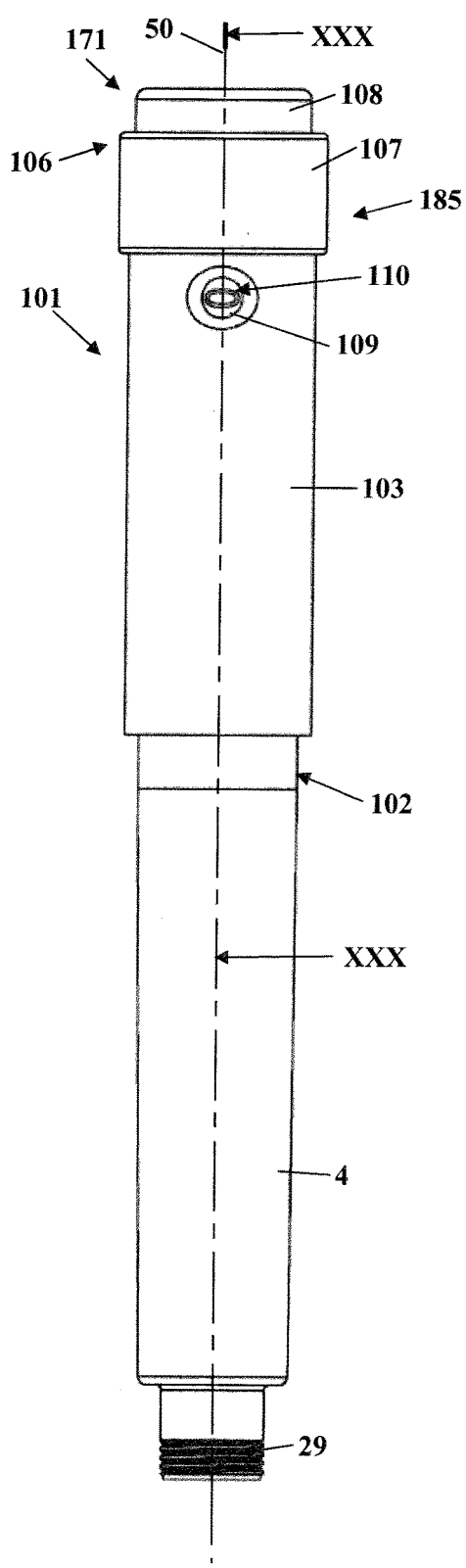
FIG. 29 shows a side view of a further embodiment of the injection device.

FIGS. 29 to 70 show an embodiment of an injection device 101. The injection device 101 has a housing 102 having an upper housing part 103, on which a holder 4 is fixed. Identical reference signs to those in the previous figures in this case identify identical elements. Arranged at the distal end of the upper housing part 103 is a control element 106 which comprises an adjustment sleeve 107 and an actuating button 108. In FIG. 29, the injection device 101 is in its zero position 185. The upper housing part 103 has a window 109, through which a scale 110 is visible. In the zero position 185, the scale shows a "0" in the embodiment. The actuating button 108 is in its distal position 171 in FIG. 29.

Figure 30:
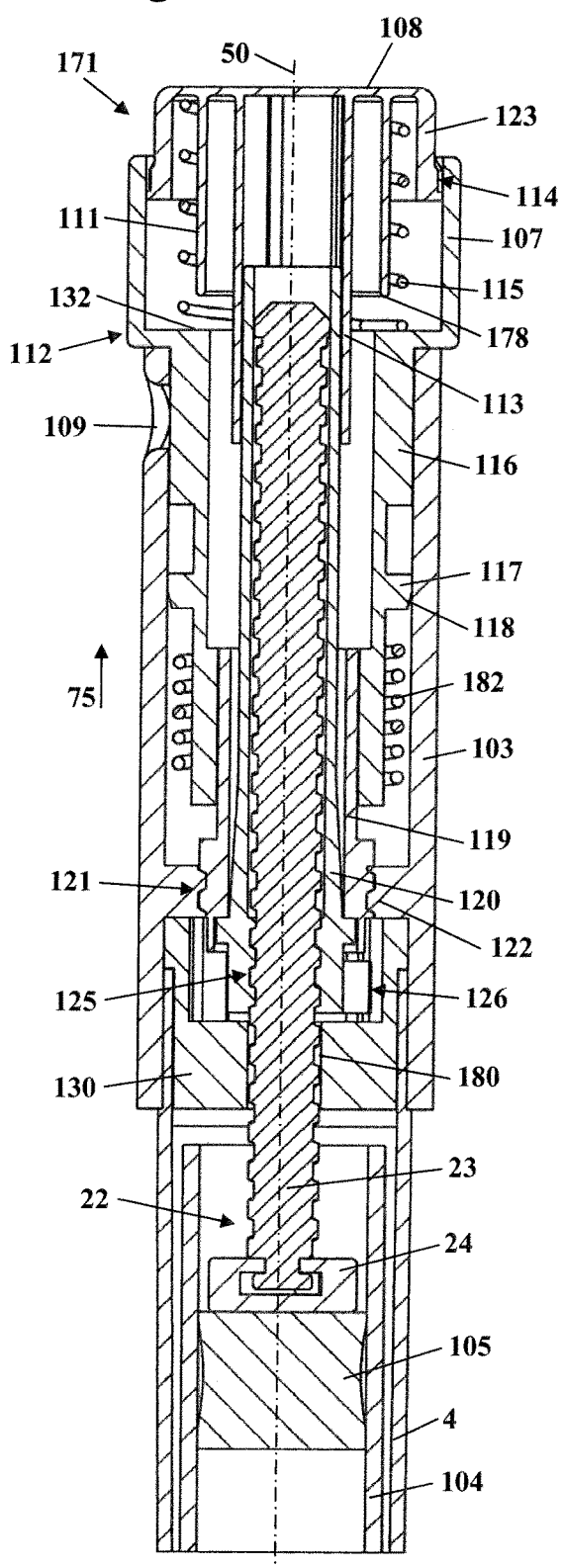
FIG. 30 shows a sectional illustration of a detail of the injection device from FIG. 29 along the line XXX-XXX in FIG. 29.

FIG. 30 shows the structure of the injection device 101 in detail. FIG. 30 also shows the container 104 inserted into the holder 4, the piston disk 24 of the dosing piston 22 bearing against the stop 105 of the container 104. The injection device 101 has a piston rod ring 130, in which the piston rod 23 is guided in a rotationally fixed manner. Via the piston rod ring 130, the piston rod 23 is held in a rotationally fixed manner with respect to the housing 102. The piston rod 23 projects through an opening 180 in the piston rod ring 130. The injection device 101 is shown in an embodiment in which the user obtains the device with the container 104 already inserted, and in which the user disposes of the injection device 101 together with the container 104 when the container 104 is empty. Replacement of the container 104 is not intended. The holder 4 is fixedly connected to the upper housing part 103, for example non-releasably snap-fastened to or glued in place in the latter. The piston rod ring 130 is secured in the upper housing part 103 in the axial direction, that is, in the direction of the longitudinal center axis 50, by the holder 4. The piston rod ring 130 is furthermore held in a rotationally fixed manner in the housing 102, as is described in more detail in the following text.

The injection device 101 has a feed part 120, which is connected to the piston rod 23 via a first threaded connection 125. Arranged at the proximal end of the feed part 120 is a latching device 126. The latching device 126 is formed between the piston rod ring 130 and the feed part 120. The feed part 120 is connected in a rotationally fixed manner to an entrainer 113. The entrainer 113 is connected in a rotationally fixed manner to the actuating button 108. In the embodiment, the entrainer 113 is integrally formed on the actuating button 108, that is, formed in one piece with the actuating button 108.

A slide 119 bears against the feed part 120, the slide 119 acting on the feed part 120 in the proximal direction. The slide 119 is connected to the upper housing part 103 via a second threaded connection 121. The second threaded connection 121 is formed at an inwardly projecting rim 122 of the upper housing part 103. The slide 119 is connected in a rotationally fixed manner to a dosing member 116. The dosing member 116 is formed in one piece with the adjustment sleeve 107 and forms a setting part 112 with the latter. The setting part 112 is mounted in the housing 102 in a rotatable but axially fixed manner. To this end, the setting part 112 has, on the dosing member 116, a rim 117 that projects radially outward and latches at the housing 102, as is described in more detail in the following text. At its proximal side, the rim 117 has a bevel 118 to make assembly easier. The scale 110 (FIG. 29) has been applied to the dosing member 116. During the setting of a quantity of injection fluid to be ejected, the adjustment sleeve 107 can be rotated through less than one revolution, such that each value on the scale 110 is assigned a clear quantity of injection fluid. In the embodiment, the adjustment sleeve 107 is rotatable through half a revolution.

The adjustment sleeve 107 is open at its distal end. The actuating button 108 is held in an axially movable manner in the adjustment sleeve 107. The actuating button 108 has a rim 123 which projects into the adjustment sleeve 107. Formed between the rim 123 and the adjustment sleeve 107 is a coupling 114. In the distal position 171, shown in FIGS. 29 and 30, of the actuating button 108, the coupling 114 is closed and connects the actuating button 108 in a rotationally fixed manner to the adjustment sleeve 107. The actuating button 108 has a cylindrical connecting piece 111, which is arranged in the radial direction between the entrainer 113 and the rim 123. The end side of the connecting piece 111 forms a stop 178, which cooperates with a shoulder 132 of the setting part 112 and, together with the shoulder 132, fixes the proximal position of the actuating button 108. Arranged on the outer side of the connecting piece 111 is a compression spring 115, which pretensions the actuating button 108 into its distal position 171.

Figure 31:
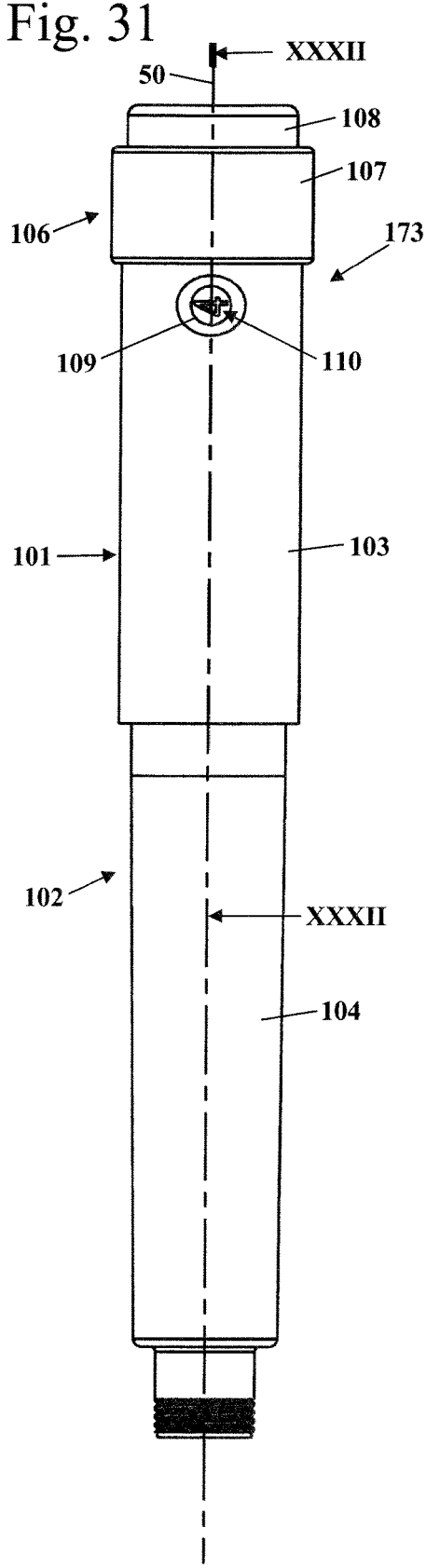
FIG. 31 shows a side view of the injection device from FIG. 1 following the setting of an intended quantity, to be ejected, of injection fluid.
Figure 32:
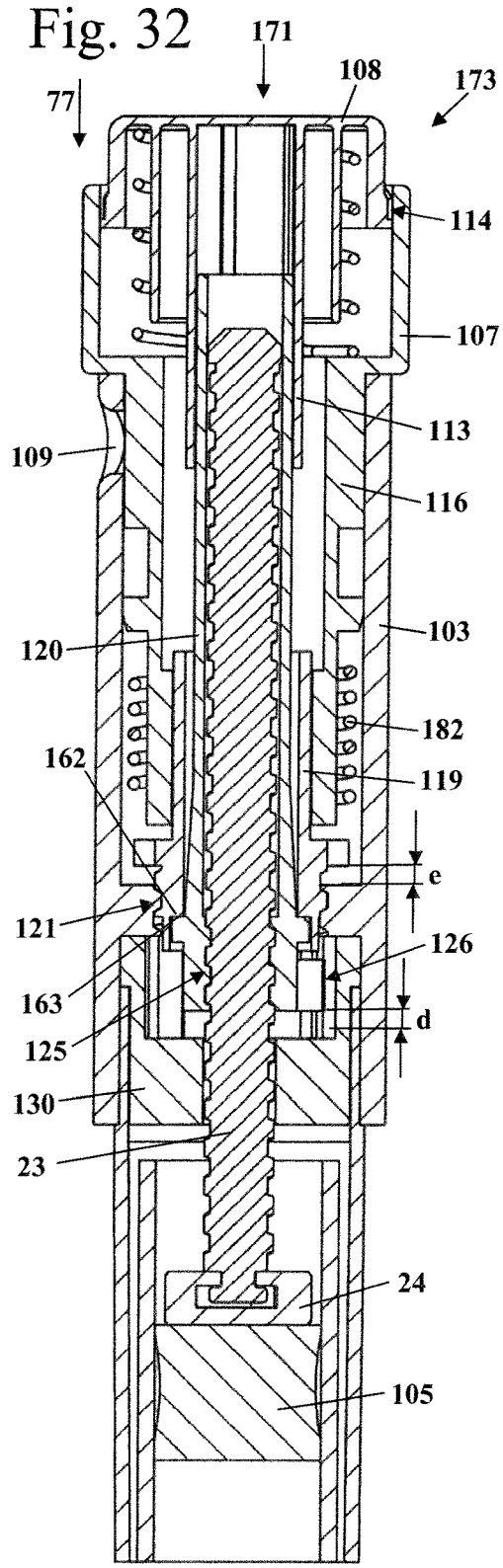
FIG. 32 shows a sectional illustration of a detail of the injection device from FIG. 31 along the line XXXII-XXXII in FIG. 31.

FIGS. 31 and 32 show the injection device 101 after the maximum dose has been set. In the window 109, the scale 110 shows the number "4". In this position, the injection device 101 is in an injection position 173, in which an intended quantity of injection fluid has been set. As FIG. 32 shows, the coupling 114 continues to be closed. The actuating button 108 is in its distal position 171. In order to set the quantity of injection fluid to be ejected, the adjustment sleeve 107 has been rotated through half a revolution in the clockwise direction with respect to the housing 102 from the position shown in FIGS. 29 and 30. In the process, the entrainer 113 has rotated the feed part 120. On account of the first threaded connection 125, the feed part 120 has moved in the distal direction, specifically by a first travel (d). The dosing member 116 has carried along and rotated the slide 119. Via the second threaded connection 121, the slide 119 has moved in the distal direction by a second travel (e), which advantageously corresponds to the first travel (d). Upon rotation of the adjustment sleeve 107, the feed part 120 rotates with respect to the housing part 103, with the result that the latching device 126 produces palpable and audible clicks.

Figure 33:
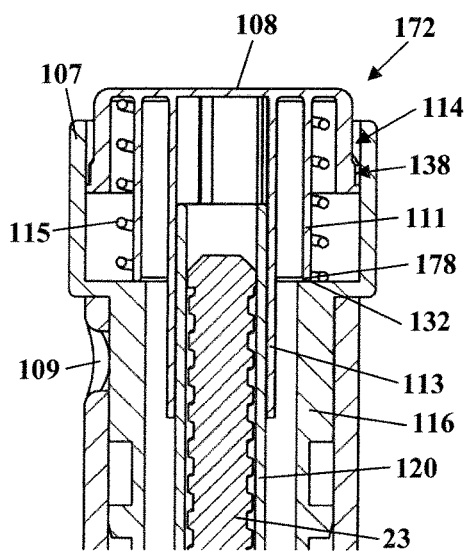
FIG. 33 shows a sectional illustration of a detail of the injection device from FIG. 31 along the line XXXII-XXXII in FIG. 31 after the actuating button has been pressed.

In order to eject the set quantity of injection fluid, the actuating button 108 has to be moved in the proximal direction in the direction of the arrow 77. The proximal direction 172 of the actuating button 108 is shown in FIG. 33. In this position, the coupling 114 is released. The actuating button 108 has an external toothing 138, which is part of the coupling 114. The external toothing 138 on the actuating button 108 has moved in the proximal direction from the region of the counterpart toothing on the adjustment sleeve 107 during the movement of the actuating button 108. As a result, the adjustment sleeve 107 is rotatable with respect to the actuating button 108. The coupling 114 is released. The actuating button 108 can be pressed until the stop 178 bears against the shoulder 132 of the dosing member 116. The stop 178 is configured such that the friction between the dosing number 116 and the actuating button 108 is low. To this end, a rounded contour is provided on the connecting piece 111 in the embodiment.

Figure 34:
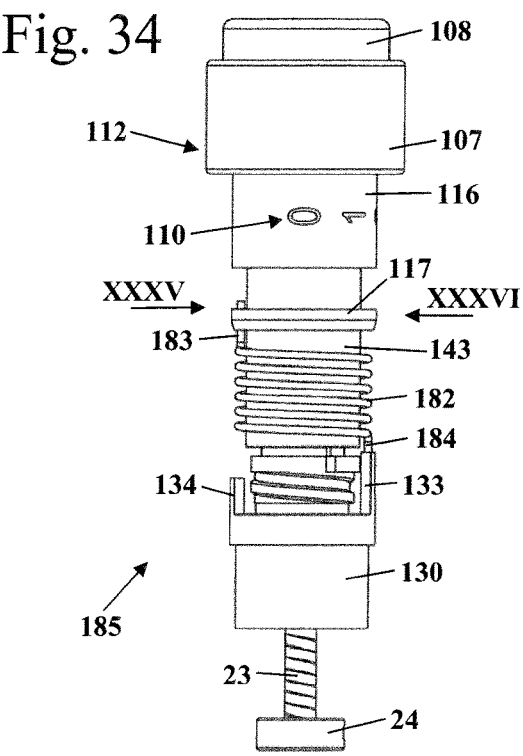
FIG. 34 shows a side view of the injection device with the housing removed.
Figure 35:
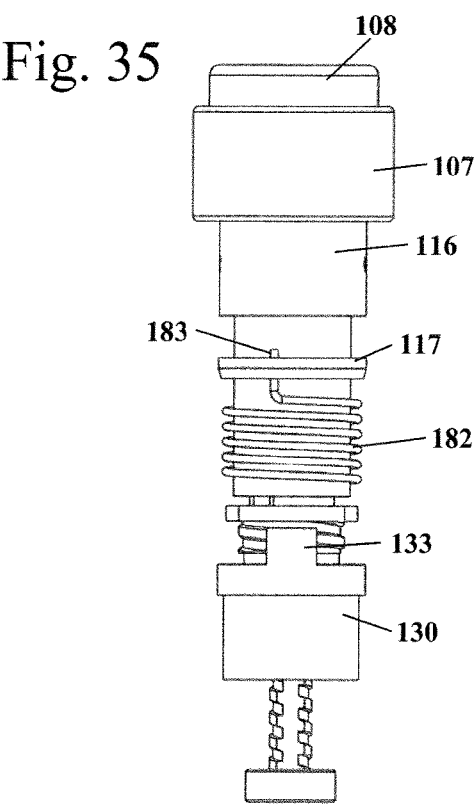
FIG. 35 shows a side view in the direction of the arrow XXXV in FIG. 34.
Figure 36:
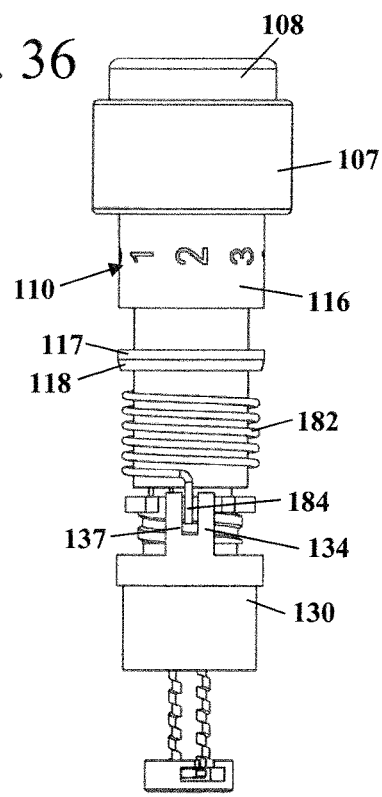
FIG. 36 shows a side view in the direction of the arrow XXXVI in FIG. 35.
Figure 37:
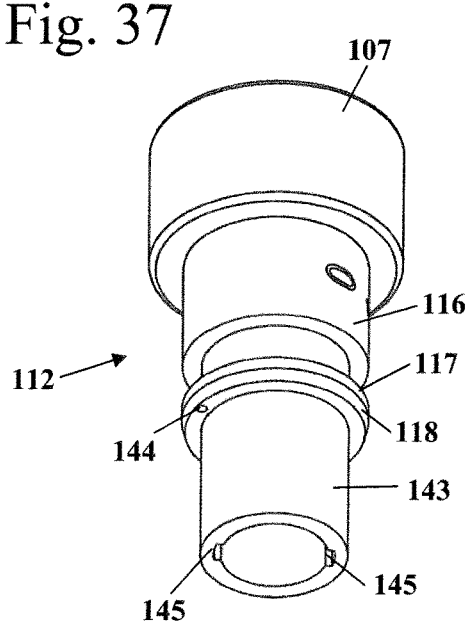
FIG. 37 shows a perspective illustration of the dosing member of the injection device from FIG. 29.

As FIGS. 34 to 36 show, a spring 182, which is configured as a torsion spring, acts between the dosing member 116 and the piston rod ring 130 that is held in a manner fixed to the housing. In the zero position 185 shown in FIGS. 34 to 36, the spring 182 has preferably already been pre-tensioned. This ensures that the spring 182 can keep the injection going right to the end, that is, can push the stopper 105 in the container 104 into the desired end position. If the adjustment sleeve 107 is rotated in the clockwise direction with respect to the piston rod ring 130, the spring 182 is tensioned further. The latching device 126 prevents the adjustment sleeve 107 from rotating back into the zero position 185 after each overcome catch. As soon as the desired dose has been set, the actuating button 108 should be pressed. As a result, the coupling 114 is released and the adjustment sleeve 107 is rotated back into its zero position 185 by the spring 182. The rotary movement of the setting part 112 with the dosing member 116 causes the slide 119 to rotate with respect to the housing part 103 and thus brings about an axial movement of the slide 119 in the proximal direction, specifically by the travel (e), via the second threaded connection 121. As FIG. 32 shows, the slide 119 has a driving ledge 162, which cooperates with a driving ledge 163 of the feed part 120 and carries along the feed part 120 in the proximal direction. In the process, the slide 119 pushes the feed part 120 by the first travel (d). The feed part 120 is supported in the circumferential direction in this case via the latching device 126, such that the feed part 120 cannot rotate. Since the piston rod 23 is held in a rotationally fixed manner in the piston rod ring 130, the piston rod 23 is moved in the proximal direction and injects the set quantity of injection fluid out of the container 104 via the stopper 105.

As FIGS. 34 to 36 show, a first end 183 of the spring 182 is mounted in the rim 117 of the dosing member 116. A second end 184 of the spring 182 is held on the piston rod ring 130. As the figures show, the piston rod ring 130 has two arms 133 and 134 which extend in a distal, axial direction on opposite sides of the piston rod ring 130. The first arm 133 has a slot 137, in which the second end 184 of the spring 182 is guided. Via the piston rod ring 130, the second end 184 of the spring 182 is connected in a rotationally fixed manner to the housing 102. During the setting of a dose, the spring 182 is tensioned, since the first end 183 is rotated with respect to the second end 184 that is held in a manner fixed to the housing. After a dose has been set, the arrangement is held in an injection position 173 via the latching device 126 until the user releases the coupling 114 by pressing the actuating button 108. Once the coupling 114 has been released, the spring 182 rotates the setting part 112 back into the zero position 185. Thus, the slide 119 is also screwed into the zero position 185 and in the process pushes the feed part 120 and thus the piston rod 23 in the proximal direction, such that the set quantity of injection fluid is ejected from the container 104.

Figure 38:
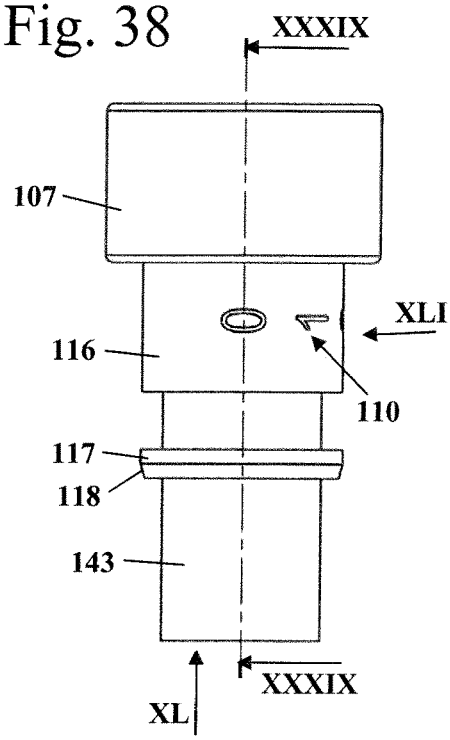
FIG. 38 shows a side view of the dosing member from FIG. 37.
Figure 39:
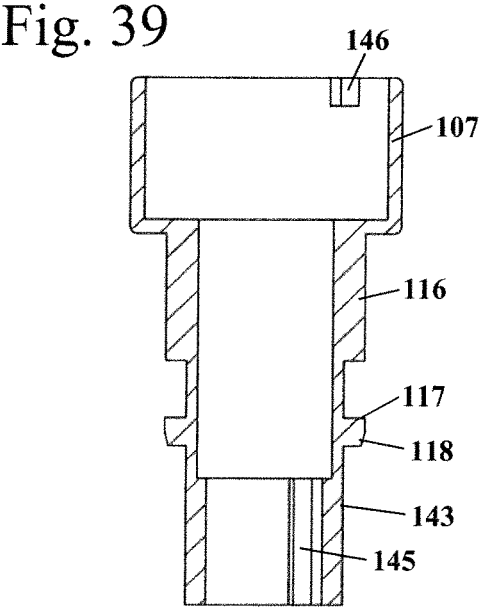
FIG. 39 shows a section along the line XXXIX-XXXIX in FIG. 38.
Figure 40:
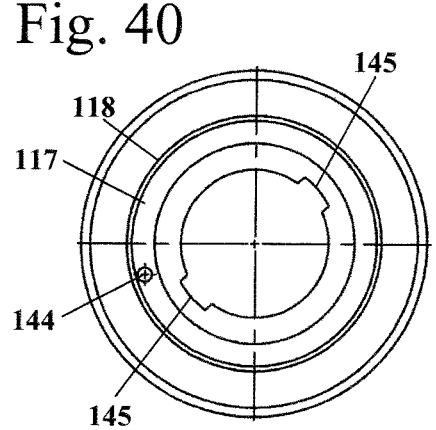
FIG. 40 shows a side view in the direction of the arrow XL in FIG. 38.

FIGS. 37 to 42 show the configuration of the setting part 112 in detail. The setting part 112 is formed in a substantially cylindrical manner and has a portion with an enlarged outside diameter, which forms the adjustment sleeve 107, and an adjoining region with a reduced outside diameter, which forms the dosing member 116. The rim 117 is adjoined by a connecting piece 143, which has the guide grooves 145 for connecting in a rotationally fixed manner to the slide 119. In the embodiment, two mutually opposite guide grooves 145 are provided. Some other number and arrangement of guide grooves 145 can also be expedient, however. The spring 182 is guided at the outer circumference of the connecting piece 143, as shown in FIG. 34. As FIG. 40 shows, the rim 117 has an opening 144 in which the first end 183 of the spring 182 is mounted.

Figure 46:
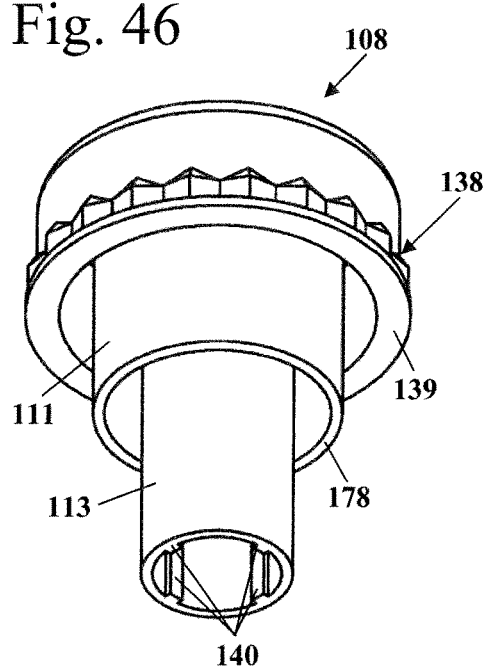
FIG. 46 shows a perspective illustration of the actuating button of the injection device from FIG. 29.
Figure 47:
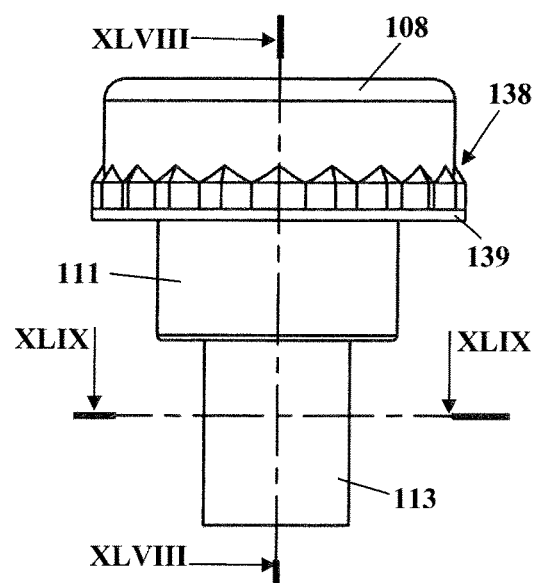
FIG. 47 shows a side view of the actuating button from FIG. 46.
Figure 48:
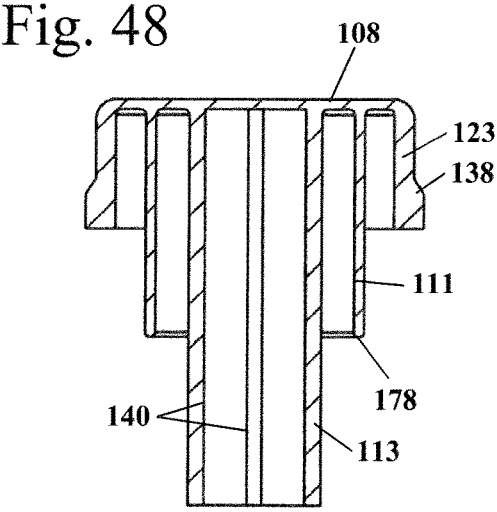
FIG. 48 shows a section along the line XLVIII-XLVIII in FIG. 47.
Figure 49:
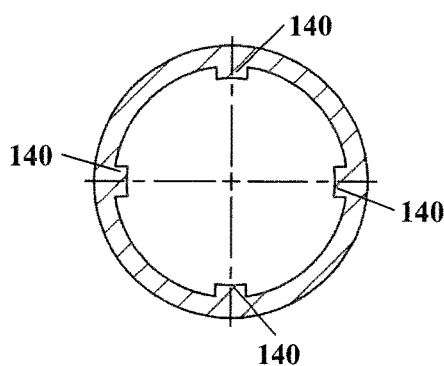
FIG. 49 shows a section along the line XLIX-XLIX in FIG. 47.

As FIG. 39 shows, a single latching tooth 146 is arranged on the inner side of the adjustment sleeve 107, the latching tooth 146 cooperating with the external toothing 138 of the actuating button 108. A larger number of latching teeth 146 can also be provided, however. Since only a single latching tooth 146 is provided, the actuating button 108 can be mounted easily in the adjustment sleeve 107 by axial insertion and latching behind the latching tooth 146. As FIG. 46 shows, the actuating button 108 has, on the distal side of the external toothing 138, a rim 139 which latches behind the latching tooth 146. In this way, the actuating button 108 is secured in the adjustment sleeve 107 in the axial direction.

Figure 41:
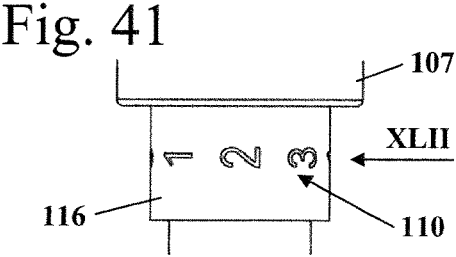
FIG. 41 shows a side view of the scale of the dosing member from FIG. 37.
Figure 42:
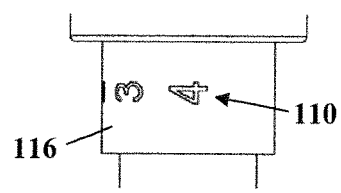
FIG. 42 shows a side view in the direction of the arrow XLII in FIG. 41.

FIGS. 38, 41 and 42 show the scale 110. The scale 110 shows a zero position 185, indicated by "0", and four injection positions 173, indicated by "1", "2", "3", and "4". The injection positions 173 are arranged at equal spacings from one another.

Figure 43:
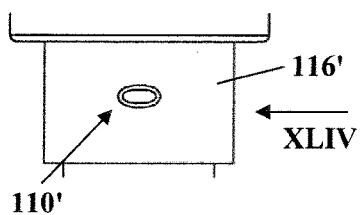
FIG. 43 shows a side view of the scale of one embodiment of the dosing member.
Figure 44:
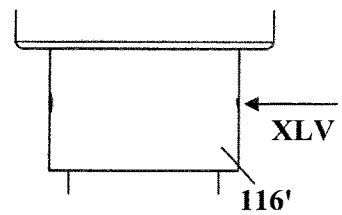
FIG. 44 shows a side view in the direction of the arrow XLIV in FIG. 43.
Figure 45:
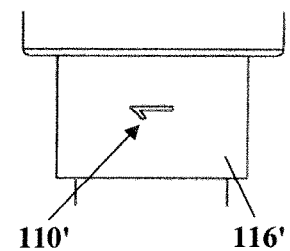
FIG. 45 shows a side view in the direction of the arrow XLV in FIG. 44.

FIGS. 43 to 45 show details of an embodiment of a dosing member 116'. The dosing member 116' has a scale 110' with a zero position 185 indicated by "0" and a single injection position 173, which is identified by "1". In the case of an injection device 101 having the dosing member 116', only a single, structurally defined quantity of injection fluid to be ejected can be set.

As FIGS. 46 to 49 show, the entrainer 113 has, on its inner side, guide ribs 140, which serve for the rotationally fixed connection to the feed part 120. In the embodiment, four guide ribs 140 that are distributed regularly around the inner circumference are provided. As FIG. 48 in particular shows, the rim 123 is shorter in the axial direction than the connecting piece 111, and the entrainer 113, which is arranged within the connecting piece 111, is longer than the connecting piece 111.

Figure 50:
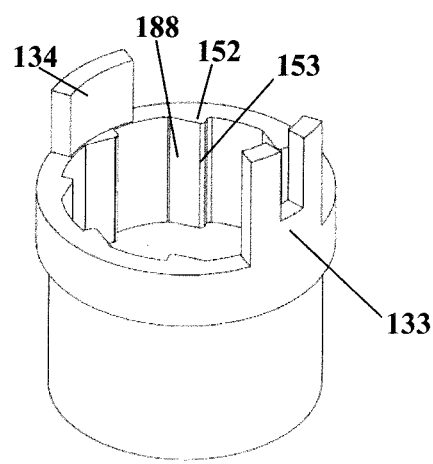
FIG. 50 shows a perspective illustration of the piston rod ring of the injection device from FIG. 29.
Figure 51:
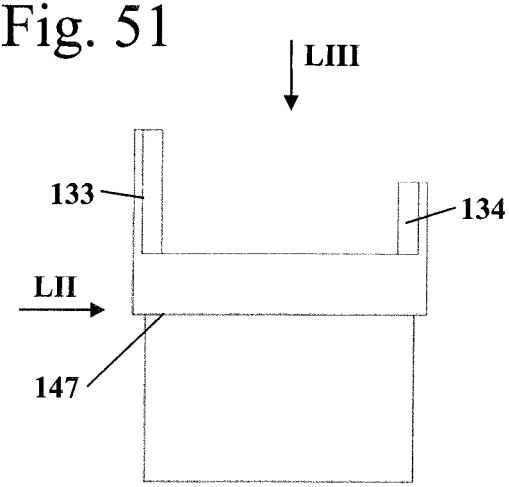
FIG. 51 shows a side view of the piston rod ring from FIG. 50.
Figure 52:
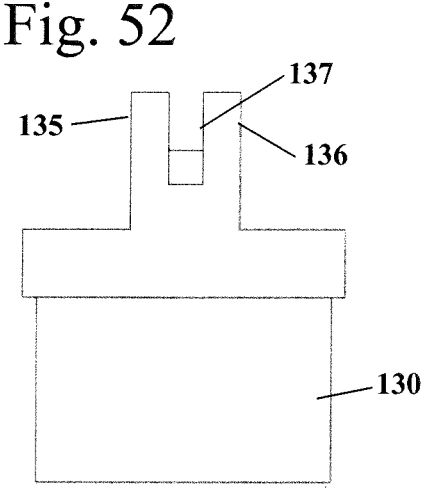
FIG. 52 shows a side view in the direction of the arrow LII-LII in FIG. 51.
Figure 53:
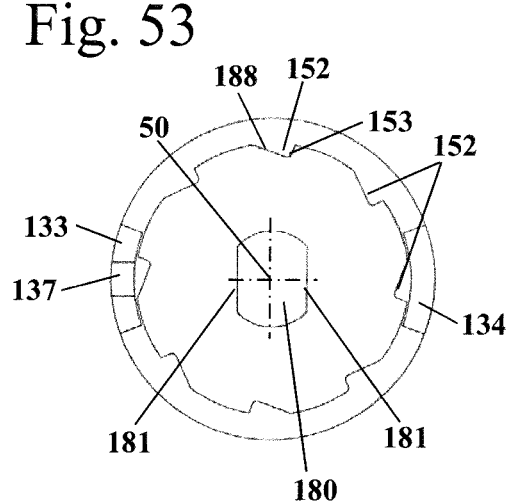
FIG. 53 shows a view from above in the direction of the arrow LIII-LIII in FIG. 51.

FIGS. 50 to 53 show the piston rod ring 130. The piston rod ring 130 has a ledge 147, against which the holder 4 bears in the mounted state and fixes the piston rod ring 130 in the housing 102 in the axial direction. As FIGS. 50 and 53 show, the piston rod ring 130 has a toothing on its inner circumference, the toothing being formed by a plurality of longitudinal ribs 152. The longitudinal ribs 152 each have a latching element 153 on one side and a slope 188 on the opposite side. The longitudinal ribs 152 are formed in an asymmetric manner. The latching elements 153 are oriented approximately in the radial direction with respect to the longitudinal center axis 50. In this way, it is not possible to rotate back into the next lowest injection position from an injection position which has already been set. However, the latching elements 153 can also be configured such that it is possible to rotate back. The latching elements 153 should be configured such that the latching elements 153 cannot be overcome simply as a result of the torque applied by the spring 182. In the embodiment, eight latching elements 153 are arranged in a manner distributed regularly around the inner circumference of the piston rod ring 130. A different number of latching elements 153 can also be advantageous in order to be able to set desired defined quantities of injection fluid.

A region in which the inner wall of the piston rod ring 130 extends in the form of a circular arc around the longitudinal center axis 50 is arranged between each of the longitudinal ribs 152. As FIG. 53 shows, the piston rod ring 130 has the opening 180 for fixing the piston rod 23 in a rotationally fixed manner. For rotationally fixed fixing, the opening 180 has side walls 181 which extend in a rectilinear manner. As FIGS. 51 and 52 show, the second arm 134 is formed in a much shorter manner than the first arm 133 in the axial direction. Formed on the first arm 133 are stops 135 and 136 with which the slide 119 cooperates. The second arm 134 does not project into the region of the stops of the slide 119.

Figure 54:
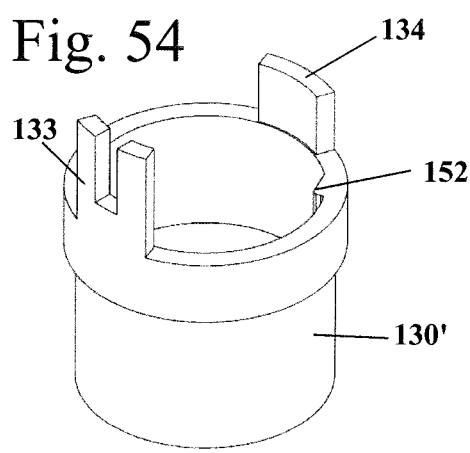
FIG. 54 shows a perspective illustration of one embodiment of a piston rod ring of the injection device from FIG. 29.
Figure 55:
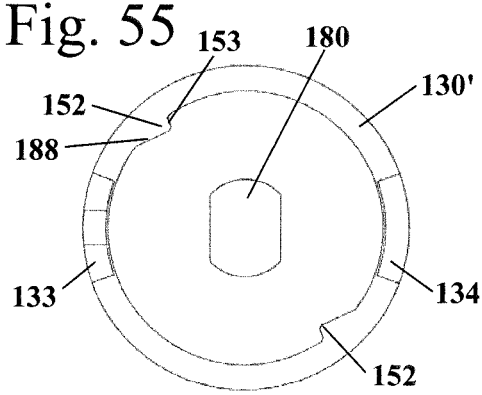
FIG. 55 shows a view of the piston rod ring from FIG. 54 from above.

FIGS. 54 and 55 show the configuration of the piston rod ring 130' for an injection device 101 in which only a single dose can be set and which can have the dosing member 116' from FIGS. 43 to 45. As FIGS. 54 and 55 show, two longitudinal ribs 152 are arranged opposite one another. The latching elements 153 and the slopes 188 are formed on the longitudinal ribs 152. In the single injection position 173, a catch 167 (FIG. 59) latches at each latching element 153.

Figure 56:
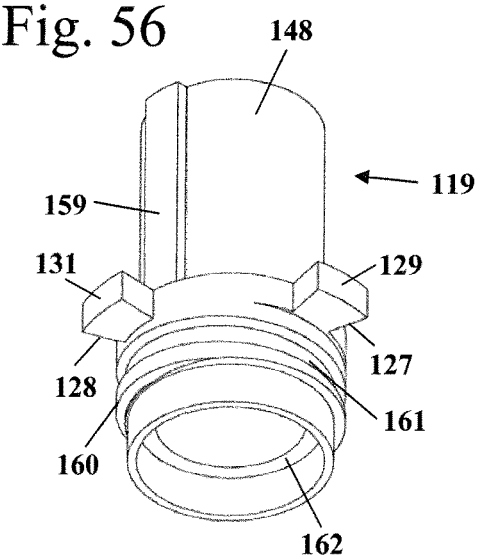
FIG. 56 shows a perspective illustration of the slide of the injection device from FIG. 29.
Figure 57:
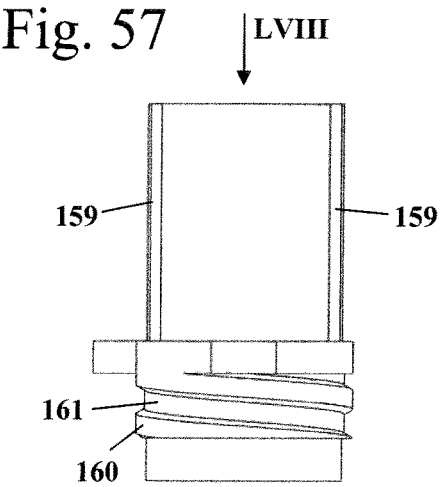
FIG. 57 shows a side view of the slide from FIG. 56.
Figure 58:
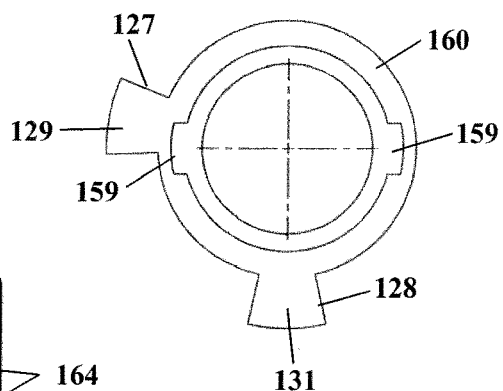
FIG. 58 shows a side view in the direction of the arrow LVIII in FIG. 57.
Figure 59:
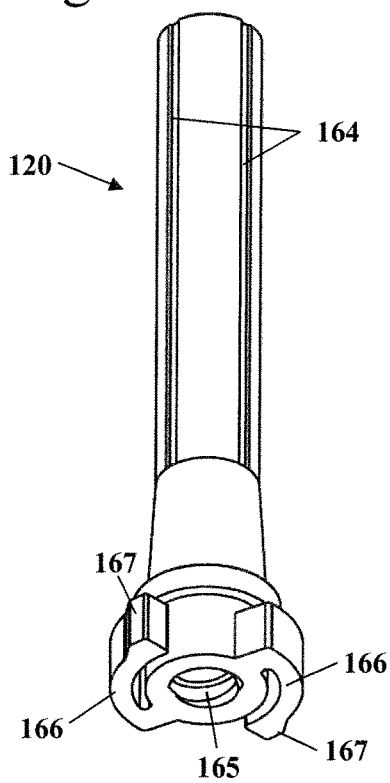
FIGS. 59 and 60 show perspective illustrations of the feed part of the injection device from FIG. 29.
Figure 60:
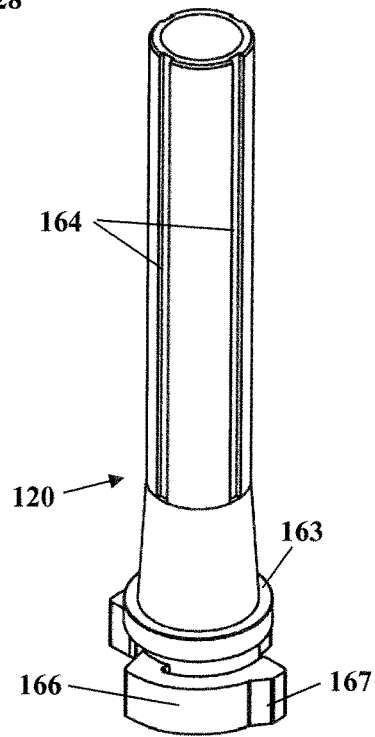

FIGS. 56 to 58 show the slide 119 in detail. The slide 119 has a cylindrical portion 148 which has longitudinal ribs 159 on its outer side, the longitudinal ribs 159 projecting into the guide grooves 145 of the dosing member 116. In this way, the slide 119 is connected in a rotationally fixed manner to the dosing member 116. On its distal side, the slide 119 has an annular rib 160 which has an external thread 161. The external thread 161 forms the second threaded connection 121 with the internal thread 151, shown in FIG. 65, of the upper housing part 103. Arranged between the annular rib 160 and the cylindrical portion 148 which bears the longitudinal ribs 159 are two arms 129 and 131 which project radially outward. Formed on the first arm 129 is a first stop 127, which cooperates with the first stop 135 of the first arm 133 of the piston rod ring 130 and defines the zero position of the injection device 101 therewith. The second arm 131 has a second stop 128, which defines the maximum dose, that is, the maximum quantity to be set of injection fluid to be ejected, with the second stop 136 of the piston rod ring 130. Between the zero position and the maximum dose, the slide 119 is rotatable through half a revolution with respect to the piston rod ring 130 in the embodiment. Other rotation ranges can also be advantageous.

FIGS. 59 to 63 show the feed part 120 in detail. The feed part 120 has a sleeve-like portion, which has longitudinal grooves 164 on its outer side. In the embodiment, four longitudinal grooves 164 are provided. The guide ribs 40 of the actuating button 108 project into the longitudinal grooves 164. In this way, the actuating button 108 and feed part 120 are connected together in a rotationally fixed manner. On its proximal side, the feed part 120 has two latching arms 166 which each bear a catch 167 at their free ends. The feed part 120 furthermore has, at its proximal end, an internal thread 165 into which the piston rod 23 is screwed, forming the second threaded connection 121 therewith. FIGS. 61 and 62 also show the driving ledge 163 against which the driving ledge 162 of the slide 119 bears.

FIGS. 64 to 66 show the upper housing part 103. The upper housing part 103 is formed in a sleeve-like manner and has the window 109 adjacently to its distal end. The inwardly projecting rim 122 has the internal thread 151. The upper housing part 103 has, on its inner side, a latching elevation 142, behind which the rim 117 of the setting part 112 (FIGS. 37 to 40) latches.

As FIG. 66 shows, the rim 122 has two openings 141 arranged opposite one another. The arms 133 and 134 of the piston rod ring 130 (FIG. 50) project through the openings 141. In this way, the piston rod ring 130 is held in the housing 102 in a rotationally fixed manner.

Figure 67:
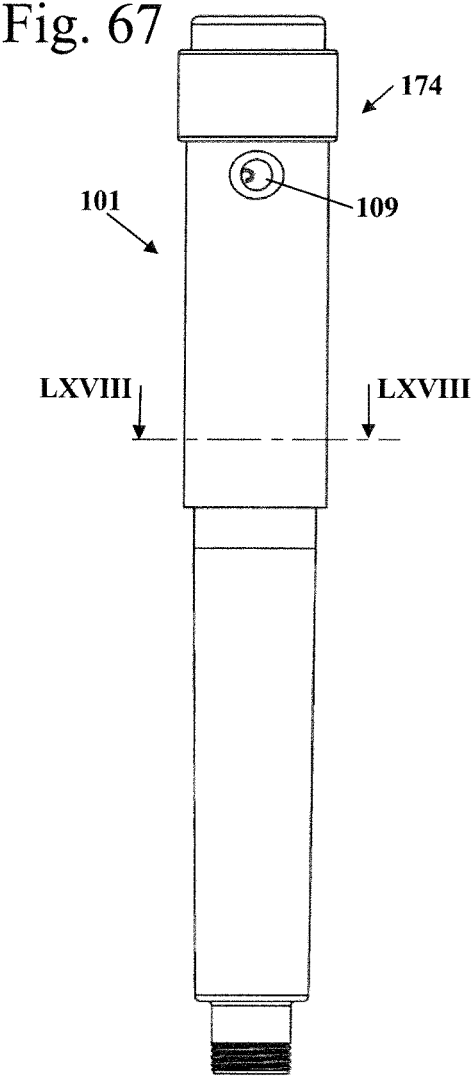
FIG. 67 shows a side view of the injection device from FIG. 29 following the setting of a non-intended quantity of injection fluid.
Figure 69:
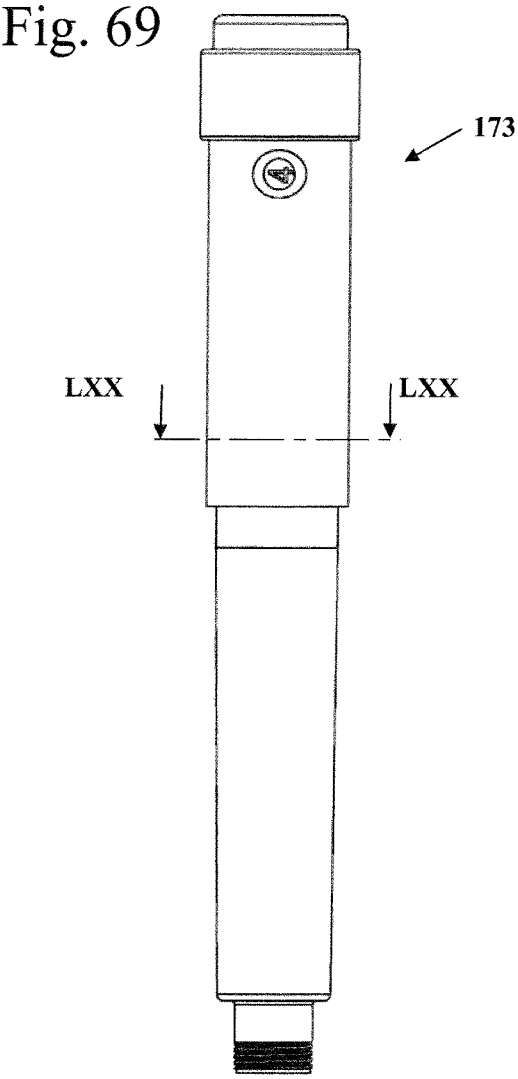
FIG. 69 shows a side view of the injection device from FIG. 29 following the setting of an intended quantity, to be ejected, of injection fluid; and, FIG. 70 shows a section along the line LXX-LXX in FIG. 69.
Figure 68:
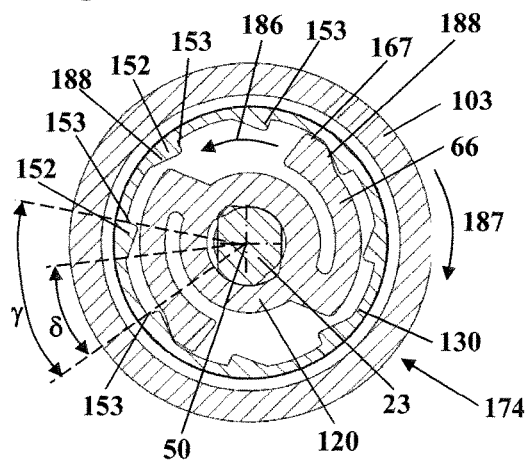
FIG. 68 shows a section along the line LXVIII-LXVIII in FIG. 67.
Figure 70:
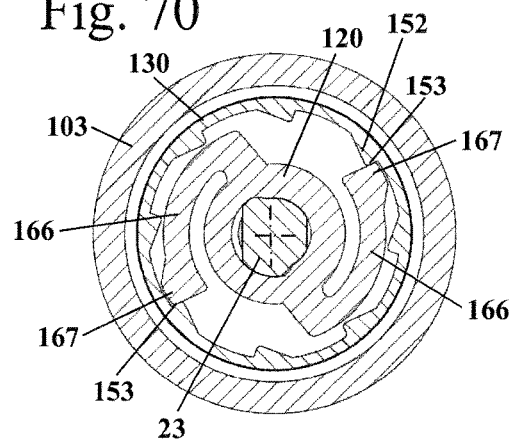

FIG. 67 shows the injection device 101 in an intermediate position 174, in which a non-intended quantity of injection fluid is set. Part of the number "3" of the scale 110 is discernible in the window 109. As FIG. 68 shows, the catches 167 are located adjacently to slopes 188 in this position. The catches 167 are not latched at latching elements 153. In this position, the spring 182 exerts a force in the direction of the arrow 186 on the feed part 120 and rotates the feed part 120 until the catches 167 bear against latching elements 153. The latching elements 153 are spaced apart from one another in the circumferential direction by an angle γ of about 45° about the longitudinal center axis 50. Adjacent longitudinal ribs 152 are at an angular spacing δ from one another which can be for example from about 20° to about 40°. The angular spacing δ corresponds to the angular range in which the dosing member 116 can be positioned in intermediate positions 174 between two injection positions 173 or an injection position 173 and the zero position 185. One intermediate position 174 is shown in FIG. 68. In intermediate positions 174, the torsion spring 182 moves the feed part 120 in the direction of the arrow 186 as soon as the user releases the adjustment sleeve 107, until the next lowest injection position 173 or the zero position 185 has been reached. In order to position the feed part 120 in an injection position 173, the user can also rotate the feed part 120 further in the direction of the arrow 187 until the injection position 173 shown in FIGS. 69 and 70 has been reached. In this position, the catches 167 bear behind latching elements 153 and are held counter to the spring force (arrow 186 in FIG. 68). The feed part 120 is guided in the axial direction along the longitudinal ribs 152 by way of the catches 167 during the ejection of a set quantity of injection fluid.

The injection device 101 is shown as a disposable injection device in which it is not possible to exchange the container 104. However, rather than the piston rod ring 130, use can also be made of a piston rod ring 30 which is held in an axially movable manner on the upper housing part and allows the container 104 to be changed.

It is understood that the foregoing description is that of the preferred embodiments of the invention and that various changes and modifications may be made thereto without departing from the spirit and scope of the invention as defined in the appended claims.

What is claimed is:

1. An injection device comprising:
a housing having a longitudinal axis;
an adjustment sleeve;
an internal tube axially and rotationally fixed to an inside portion of the housing;
a dosing member threadedly connected to the housing such that rotation of the adjustment sleeve during dose setting causes rotation of the dosing member relative to the housing and the internal tube, and simultaneously moves the dosing member axially in a distal direction;
a latching device comprising two longitudinal ribs and a catch, where engagement of the catch with one of the longitudinal ribs defines an intended set dose and where rotation of the dosing member to positions where the catch is not engaged with one of the longitudinal ribs defines unintended doses; and,
a torsion spring acting between the dosing member and the internal tube, where if during dose setting rotation of the adjustment sleeve is stopped at an unintended dose the torsion spring will cause the dosing member to return to a previous intended set dose.

2. The injection device of claim 1, where the two longitudinal ribs are rotationally fixed relative to the housing during dose setting and dose delivery, and the catch is rotatable relative to the two longitudinal ribs.

3. The injection device of claim 1 further comprising a piston rod threadedly engaged with a feed part, wherein the threaded engagement comprises a first thread on the piston rod and a second thread on the feed part, and wherein the first thread and the second thread each have a defined pitch.

4. The injection device of claim 3 where the threaded engagement of the feed part with the piston rod is configured such that rotation of the dosing member during dose setting causes the feed part to rotate relative to the piston rod and to move distally relative to the piston rod.

5. The injection device of claim 3 where the feed part does not rotate during dose delivery.

6. The injection device of claim 3 where the piston rod does not rotate during dose delivery.

7. The injection device of claim 3 where the threaded connection between the housing and dosing member has a pitch that is greater than the defined pitch of the threaded connection between the piston rod and the feed part.

8. The injection device of claim 1 where the dosing member comprises a groove extending helically around an outer circumference of the dosing member that defines part of the threaded connection to the housing.

9. The injection device of claim 1 further comprising an actuating button.

10. The injection device of claim 9 further comprising a compression spring that presses the actuating button into a first position.

11. The injection device of claim 3 where the piston rod further comprises two flattened portions on opposite longitudinal sides from two threaded portions.

12. The injection device of claim 3 where the piston rod further comprises a distal end having a last dose stop configured to engage with the feed part to prevent the setting of a dose greater than an amount of injection fluid remaining in the injection device.

13. The injection device of claim 1 where the catch and the two longitudinal ribs are configured to allow relative rotation to each other such that an intended dose can be canceled.

14. The injection device of claim 1 where the catch is directed radially outward from the longitudinal axis.

15. An injection device comprising:
a housing having a longitudinal axis;
an adjustment sleeve;
an internal tube axially and rotationally fixed to an inside portion of the housing;
a dosing member threadedly connected to the housing such that rotation of the adjustment sleeve during dose setting causes rotation of the dosing member relative to the housing and the internal tube, and simultaneously moves the dosing member axially in a distal direction;
a latching device comprising two longitudinal ribs and a catch, where engagement of the catch with one of the longitudinal ribs defines an intended set dose and where rotation of the dosing member to positions where the catch is not engaged with one of the longitudinal ribs defines unintended doses;
a torsion spring acting between the dosing member and the internal tube, where if during dose setting rotation of the adjustment sleeve is stopped at an unintended dose the torsion spring will cause the dosing member to return to a previous intended set dose; and,
a piston rod threadedly engaged with a feed part, wherein the threaded engagement comprises a first thread on the piston rod and a second thread on the feed part, wherein the first thread and the second thread each have a defined pitch, where the threaded connection between the housing and dosing member has a pitch that is greater than the defined pitch of the threaded connection between the piston rod and the feed part.

* * * * *